(12) United States Patent
Burgos et al.

(10) Patent No.: US 10,786,522 B2
(45) Date of Patent: Sep. 29, 2020

(54) COMPOSITIONS THAT INCLUDE ANTHOCYANIDINS AND METHODS OF USE

(75) Inventors: Rafael Burgos, Valdivia (CL); Juan Hancke, Region Metropolitana (CL); Evelyn Jara, Valdivia (CL); Maria Hidalgo, Valdivia (CL)

(73) Assignee: Maqui NewLife S.A., Santiago (CL)

( * ) Notice: Subject to any disclaimer, the term of this patent is extended or adjusted under 35 U.S.C. 154(b) by 1570 days.

(21) Appl. No.: 13/076,117

(22) Filed: Mar. 30, 2011

(65) Prior Publication Data
US 2011/0268825 A1 Nov. 3, 2011

Related U.S. Application Data

(63) Continuation of application No. PCT/IB2010/002698, filed on Oct. 21, 2010.

(60) Provisional application No. 61/253,835, filed on Oct. 21, 2009, provisional application No. 61/279,541, filed on Oct. 22, 2009.

(51) Int. Cl.
| | |
|---|---|
| *A61K 31/7048* | (2006.01) |
| *A61K 9/48* | (2006.01) |
| *A61K 31/22* | (2006.01) |
| *A61K 31/341* | (2006.01) |
| *A61K 31/365* | (2006.01) |
| *A61K 31/41* | (2006.01) |
| *A61K 45/06* | (2006.01) |
| *A23L 33/105* | (2016.01) |
| *A61K 31/216* | (2006.01) |
| *A61K 31/352* | (2006.01) |
| *A61K 38/13* | (2006.01) |

(52) U.S. Cl.
CPC ........ *A61K 31/7048* (2013.01); *A23L 33/105* (2016.08); *A61K 9/4816* (2013.01); *A61K 9/4866* (2013.01); *A61K 9/4875* (2013.01); *A61K 31/216* (2013.01); *A61K 31/22* (2013.01); *A61K 31/341* (2013.01); *A61K 31/352* (2013.01); *A61K 31/365* (2013.01); *A61K 31/41* (2013.01); *A61K 38/13* (2013.01); *A61K 45/06* (2013.01); *A23V 2002/00* (2013.01)

(58) Field of Classification Search
CPC .................................................. A61K 31/7048
See application file for complete search history.

(56) References Cited

U.S. PATENT DOCUMENTS

2009/0176718 A1   7/2009   Ribnicky et al.

FOREIGN PATENT DOCUMENTS

| EP | 1 074 254 | 2/2001 |
|---|---|---|
| EP | 1 683 805 | 7/2006 |
| EP | 1 882 473 | 1/2008 |
| JP | 2008239612 A * | 10/2008 |
| WO | WO1997/41137 | 11/1997 |
| WO | WO2001/15553 | 3/2001 |
| WO | WO 03080062 A1 * | 10/2003 |
| WO | WO2007/038421 | 4/2007 |
| WO | WO2008/016593 | 2/2008 |
| WO | WO2008/126980 | 10/2008 |
| WO | WO2009/059218 | 5/2009 |
| WO | WO2010/131049 | 11/2010 |

OTHER PUBLICATIONS

Nizamutdinova et al., "Anthocyanins from black soybean seed coats stimulate wound healing in fibroblasts and keratinocytes and prevent inflammation in endothelial cells," Food and Chemical Toxicology, Pergamon, GB 47:2806-2812 (2009).

Escribano-Bailon et al., "Anthocyanins in berries of Maqui," Phytochemical Analysis: PCA 2006 Pubmed, 17:8-14 (2006).

Thomas et al., "Pharmacokinetics of anthocyanidin-3-glycosides following consumption of *Hibiscus sabdariffa* L. extract," Journal of Clinical Pharmacology, 45:203-210 (2005).

Grace et al., "Hypoglycemic activity of a novel anthocyanin-rich formulation from lowbush blueberry, Vaccinium angustifolium Aiton," Phytomedicine, Gustav Fischer Verlag, Stuttgart, DE 16:406-415 (2009).

Burns et al., "Phytochemical composition and metabolic performance-enhancing activity of dietary berries traditionally used by Native North Americans," Journal of Agricultural and Food Chemistry, 56:654-660 (2008).

Konstantin et al., "Anthocyanins from black soybean seed coats inhibit UVB-induced inflammatory cyclooxygenase-2 gene expression and PGE2 production through regulation of the nuclear factor-kappaβ and phosphatidylinositol 3-kinase/Akt pathway," Journal of Agricultural and Food Chemistry, 56:8969-8974 (2008).

Christian et al., "Antioxidant and cyclooxygenase inhibitory activity of sorrel (*Hibiscus sabdariffa*)," Journal of Food Composition and Analysis, Academic Press, 19:778-783 (2006).

Segura-Carretero et al., "Selective extraction, separation, and identification of anthocyanins from *Hibiscus sabdariffa* L. using solid phase extraction-capillary electrophoresis-mass spectrometry (time-of-flight / ion trap)," Electrophoresis, 29:2852-2861 (2008).

Diouf et al., "Study on chemical composition, antioxidant and anti-inflammatory activities of hot water extract from Piceamariana bark and its proanthocyanidin-rich fractions," Food Chemistry, 113:897-902 (2009).

(Continued)

*Primary Examiner* — Amy L Clark
(74) *Attorney, Agent, or Firm* — Pharmaceutical Patent Attys LLC

(57) ABSTRACT

The compositions described herein and featured in the present invention include those that comprise anthocyanidin combinations rich in delphinidins, including delphinidins such as the ones found in berries. The compositions can optionally include either compositions that comprise andrographolides, such as the ones found in a plant of the genus *Andrographis*, or compositions that comprise combinations of myrtillin, quercetin, or caffeoyl quinic derivatives and proanthocyanidins, such as the ones found in the herba of a plant of the genus *Vaccinium*.

6 Claims, 5 Drawing Sheets

(56) References Cited

OTHER PUBLICATIONS

Kwon et al., "Delphinidin suppresses ultraviolet β-induced cyclooxygenases-2 expression through inhibition of MAPKK4 and PI-3 kinase," Carcinogenesis, 30:1932-1940 (2009).

Hwang Mun Kyung et al., "Fyn kinase is a direct molecular target of delphinidin for the inhibition of cyclooxygenase-2 expression induced by tumor necrosis factor-alpha," Biochemical Pharmacology, 77:1213-1222 (2009).

Schreckinger et al., "Antioxidant Capacity and in Vitro Inhibition of Adipogenesis and Inflammation of Phenolic Extracts of Vaccinium floribundum and Aristotelia chilensis," Journal of Agricultural and Food Chemistry, 58:8966-8976 (2010).

* cited by examiner

COMPOSITIONS THAT INCLUDE ANTHOCYANIDINS AND METHODS OF USE

CROSS REFERENCE TO RELATED APPLICATIONS

This application is continuation of International Application No. PCT/IB2010/002698, filed on Oct. 21, 2010, which claims the benefit of U.S. Provisional Patent Application No. 61/253,835, filed Oct. 21, 2009, and U.S. Provisional Patent Application No. 61/279,541, filed Oct. 22, 2009. The entire content of these earlier filed applications is hereby incorporated by reference in the present application.

TECHNICAL FIELD

This invention relates to various compositions that generally include certain amounts and types of anthocyanidins and/or their glycoside counterparts. These compositions can be made and used alone or made and used in combination with other compositions, for example, those containing an andrographolide. The compositions can be formulated as pharmaceutical preparations or incorporated into foods such as drinks and cereal bars. Their administration or consumption helps maintain immune function, stimulates the immune system, reduces inflammation, and protects against other unwanted conditions (e.g., metabolic syndrome).

BACKGROUND OF THE INVENTION

Anthocyanidins and anthocyanins (anthocyanidins including sugar groups) are a large family of naturally occurring pigments. The color of most fruits, flowers and berries is determined by their content of anthocyanidins and anthocyanins.

Others have suggested uses for anthocyanidins. For example, it has been suggested that anthocyanidins and anthocyanidin derivates can exhibit antiviral effects in infected cells and antineoplastic effects in neoplastic cells (see PCT/NO97/00100 (WO 97/41137)). Anthocyanin-rich extracts are also disclosed for the treatment of a disordered metabolism syndrome (see U.S. Application Publication No. 2009/0176718).

SUMMARY

The present invention is based, in part, on our studies of compositions that include an anthocyanin or anthocyanidin preparation that is rich in delphinidin(s). While there has been significant interest in anthocyanins and in the antioxidant properties of berry extracts, this is, to our knowledge, the first description of compositions that include not only a certain amount of anthocyanins and/or anthocyanidins, but also a certain amount and/or a certain type of a delphinidin. The various compositions and methods of the invention have other distinguishing characteristics as well.

In a first aspect, the compositions of the present invention include one or more anthocyanidins and/or aglycolic anthocyanins that have been enriched for one or more delphinidins. For example, either the amount or type of the anthocyanidins or anthocyanins or the amount or type of the delphinidins (or both) may differ from (e.g., exceed) that found in a naturally occurring composition such as a berry or other plant part or product. In embodiments of the invention, the delphinidin-containing (e.g., delphinidin-rich) compositions can include additional specific compounds such as an adrographolide (e.g., from a plant of the genus Andrographis). In embodiments of the invention, the delphinidin-containing (e.g., delphinidin-rich) compositions can include specific compounds such as one or more of: myrtillin, cyanidin, quercetin, a caffeoylquinic derivative, a proanthocyanidin and/or proanthocyanin (e.g., as found in the herba (e.g., leaves) of a plant of the genus Vaccinium).

More specifically, the invention features compositions that consist of or that include a plurality of anthocyanins and/or anthocyanidins in which (a) at least or about 35% of the composition, by weight, is an anthocyanin or anthocyanidin and (b) at least or about 15% of the anthocyanins and/or anthocyanidins, by weight, are sugar-free or sugar-containing delphinidins. These compositions and any of the compositions of the invention can be non-toxic, and all are non-naturally occurring (i.e., none are identical to a product of nature). As noted, the compositions can include sugar-containing delphinidin, such as a delphinidin glucoside (e.g., delphinidin-3-O-sambubioside-5-O-glucoside). The amount of the delphinidin can vary according to the parameters set out herein. For example, at least or about 15% of the anthocyanins and/or anthocyanidins, by weight (e.g., at least or about 15%, 20%, 25%, 30%, 35%, 40%, 45%, or 50%), can be a delphinidin such as delphinidin-3-O-sambubioside-5-O-glucoside. Expressed differently, at least or about 5% of the composition as a whole, by weight (e.g., at least or about 5%, 10%, 15%, 20%, or more), can be a delphinidin such as delphinidin-3-O-sambubioside-5-O-glucoside.

In the compositions of the invention, one or more, including all, of the anthocyanins or anthocyanidins can conform to the following formula:

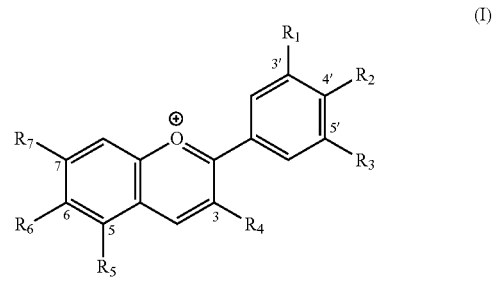

(I)

wherein each of $R_1$, $R_2$, $R_3$, $R_4$, $R_5$, $R_6$, and $R_7$ are, independently, —H, —OH, or $OCH_3$ (see Table 1, below).

While specific formulations are discussed further below, and while formulation methods, including those for other anthocyanidin-containing preparations are known in the pharmaceutical and food industry arts, we note here that the compositions of the invention can be formulated for oral consumption (e.g., as an ingredient of a food product) or oral administration (e.g., as a tablet, pill, capsule, caplet, and the like), or they can be formulated for administration by a parenteral route.

The compositions of the invention (as described above and further below) can also include an andrographolide and can be enriched for andrographolides (e.g., the andrographolide can constitute, by weight, at least or about 10% (e.g., at least or about 10%, 15%, 20%, 25%, 30% or more) of the composition. The andrographolide can be an andrographolide, a deoxyandrographolide, a neoandrographolide, or a mixture thereof, and it may be contained within an extract of a plant of the genus Andrographis (e.g., Andrographus paniculata). The amount of the andrographolide may also be expressed relative the amount of the anthocyanins and/or anthocyanidins, and the ratio of anthocyanin and/or anthocyanidin to andrographolide can be about 1.0:0.1 to about 1.0:10 (w:w) (e.g. 1.0:0.5 to about 1.0:2.5 (w:w)).

Compositions that include (e.g., compositions enriched for) myrtillin, quercetin, and/or cyanidin can include at least or about 15% (e.g., at least or about 15%, 20%, 25%, 30%, or more) myrtillin, quercetin, and/or cyanidin.

Where a composition of the invention includes a proanthocyanin or proanthocyanidin, it can be one extracted from a plant of the genus *Vaccinium* (e.g., *Vaccinium augustifolium* and/or *Vaccinium myrtillus*).

Where a composition of the invention includes a caffeoylquinate derivative, it can be chlorogenate or chlorogenic acid.

As with other components, the amounts of proanthocyanins and/or proanthocyanidins can be expressed relative to the anthocyanins and/or anthocyanidins. For example, the ratio of the plurality of anthocyanins and/or anthocyanidins to the proanthocyanin and/or proanthocyanidin can be is about 1.0:0.1 to about 1.0:10 (w:w) (e.g., about 1.0:0.5 to 1.0:2.5 (w:w)). Where a caffeoylquinate is present, the ratio of the plurality of anthocyanins and/or anthocyanidins to the caffeoylquinate derivative can also be about 1.0:0.1 to about 1.0:10 (w:w) (e.g., about 1.0:0.5 to 1.0:2.5 (w:w)).

In more specific embodiments, the pharmaceutical compositions of the invention can include (a) a first composition comprising a carrier and (b) about 100 mg to 400 mg of a second composition comprising one or more anthocyanins and/or anthocyanidins, wherein the anthocyanins and/or anthocyanidins constitute at least 35% of the first composition and at least 15% of the anthocyanins and/or anthocyanidins are sugar-free or sugar-containing delphinidins. The first composition can include microcrystalline cellulose, lactose, silicon dioxide, glyceryl monostearate, soya lecithin, or *Oenothera biennis* oil. In another specific embodiment, the pharmaceutical compositions described above can include about 35%-45% of a second composition containing an anthocyaninin or anthocyanidin and about 15-50% of the anthocyaninins or anthocyanidins can be sugar-free or sugar-containing delphinidins.

The pharmaceutical compositions can also include a third composition comprising an andrographolide (e.g., about 30-40% of the third composition is an andrographolide). The ratio of the second composition comprising the anthocyaninins or anthocyanidins to the third composition comprising the andrographolide can be about 1.0:0.5 to 1.0:3.0 (w:w). As noted, the compositions can be formulated as capsules (e.g., as a soft cellulose capsule or hard gelatine capsule).

In another specific embodiment, the invention features pharmaceutical compositions comprising: 100-400 mg of a first composition comprising anthocyanidins, wherein about 41% of the first composition is an anthocyanin or anthocyanidin and about 35% of the anthocyanins or anthocyanidins are sugar-free or sugar-containing delphinidins; 300 mg of a second composition comprising an andrographolide, wherein about 35% of the second composition is the andrographolide; and a third composition comprising a carrier, wherein the third composition, optionally, includes one or more of glyceryl monostearate, soya lecithin, *Oenothera biennis* oil, microcrystalline cellulose, lactose, silicon dioxide, povidone, and sodium carboxymethylcellulose. The third composition can include 30 mg of glyceryl monostearate, 20 mg of soya lecithin, and 700 mg *Oenothera biennis* oil; 400 mg of microcrystalline cellulose, 95 mg of lactose, and 10 mg of silicon dioxide; or 400 mg microcrystalline cellulose, 15 mg povidone, and 10 mg sodium carboxymethylcellulose.

In another specific embodiment, the pharmaceutical compositions can include (a) a first composition comprising a carrier, (b) about 100 mg to 400 mg of a second composition comprising one or more anthocyanins and/or anthocyanidins, wherein the anthocyanins and/or anthocyanidins constitute at least 35% of the first composition and at least 15% of the anthocyanins and/or anthocyanidins are sugar-free or sugar-containing delphinidins, and (c) a third composition comprising caffeeoylquinic acid.

The compositions described above and further below, can be used in various treatment and prophylactic methods. In one aspect, the invention features methods of maintaining immune function in a subject by, inter alia, administering to the subject a composition as described herein, and the subject may have no overt condition known to compromise the immune system. The composition can be administered in an amount and for a time sufficient to maintain immune function. In any of the present methods, the subject can be a human, although the invention is not so limited, and any of the present methods can be expressed in terms of a "use" of the compositions. For example, the method just described can be expressed as use of a compositions as described herein for the preparation of a medicament (e.g., the preparation of a medicament for use in maintaining immune function). The methods can further include a step of prescribing, for the subject, dietary standards and/or an exercise program.

A subject to be treated can be an animal kept as a domestic pet or as livestock, and where the subject is an animal kept as livestock, the administration of the composition may reduce or obviate the need for prophylactic antibiotic treatment. Livestock includes, inter alia, a cow, sheep, pig, chicken, turkey, or duck.

The invention features methods of treating a patient who has a condition in which the immune system is undesirably suppressed by administering a composition as described herein in an amount and for a time sufficient to stimulate the patient's immune system. The patient can be a human and the condition can be cancer or an acquired immunodeficiency syndrome.

The invention features methods of treating inflammation in a subject by administering to the subject a composition as described herein in an amount and for a time sufficient to reduce or improve a sign or symptom of inflammation in the subject. The subject can be a human and the inflammation can be caused by a burn or other traumatic injury, a chemical irritant or toxin, an infection (e.g., a bacterial or viral infection), or an autoimmune disease.

The invention features methods of treating metabolic syndrome in a patient by administering to the subject a composition as described herein in an amount and for a time sufficient to reduce or improve a sign or symptom of metabolic syndrome in the patient. The patient can be a human, and the metabolic syndrome can be associated with diabetes or Syndrome X, or CHAOS.

The details of one or more embodiments of the invention are set forth in the accompanying drawings and the description below. Other features, objects, and advantages of the invention will be apparent from the description and drawings, and from the claims.

DETAILED DESCRIPTION

Figure 1:
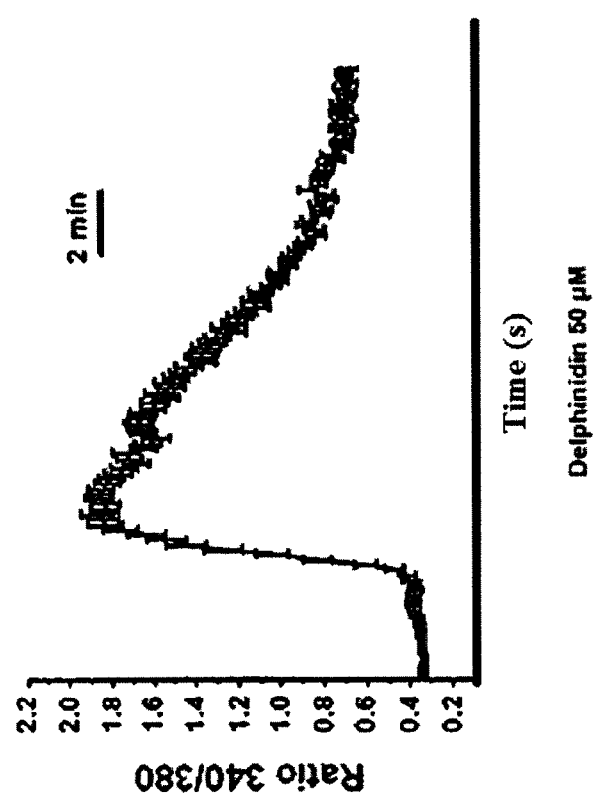
FIG. 1 shows the average spectrofluorescence results for 4 measurements of calcium fluxes in Jurkat T cells treated with compositions of delphinidin.

The invention features a number of compositions that comprise anthocyanidins, more preferably delphinidins, alone or combined with other compositions that comprise compounds selected among andrographolides, caffeoyl quinic derivatives and proanthocyanidins. As described further below, the compositions can be formulated in various ways. For example, formulations within the invention include the compositions per se, compact oral formulations (e.g., capsules or "gel tabs" including the extracts and a carrier), and food products (e.g., juices or cereal bars). In addition, the invention features methods of using these compositions to stimulate the immune system of a subject, to maintain immune function in a subject who does not have an overt condition (i.e., to promote or maintain immune function in a seemingly healthy person (e.g., a person who has not been diagnosed with an infection or immune disease)), treat a subject who has a recognizable condition (e.g., an infection), treat an inflammation condition in a subject or to improve a sign or symptom of metabolic syndrome.

The terms "treat" or "treating" refer to accomplishing one or more of the following: (a) reducing the severity of a disorder; (b) limiting the development of symptoms characteristic of the disorder(s) being treated; (c) limiting worsening of symptoms characteristic of the disorder(s) being treated; (d) limiting recurrence of the disorder(s) in subjects that have previously had the disorder(s); and (e) limiting recurrence of symptoms in subjects that were previously symptomatic for the disorder(s). Any of the present methods can include a step of identifying a patient in need of treatment. For example, a subject can be examined and/or subjected to clinical tests in order to determine whether they have, for example, a metabolic disorder or inflammation. Among the conditions amenable to treatment are metabolic disorders such as Syndrom X, insulin resistance syndrome, Reaven's sydrome, and the syndrome referred to as CHAOS. Diabetes can also be treated.

More specifically, the invention features compositions that comprise anthocyanidin combinations rich in delphinidins. In one embodiment, the compositions include one or more compounds found within a plant extract (i.e., where the compositions are based on the extracts but are not extracts per se), the compositions can include some or all of the anthocyanidins naturally found within the extract. For example, the composition (e.g., a nutriceutical or food product) can include some, most, or all of the anthocyanidins naturally present in an extract. The anthocyanidin can conform to the following formula:

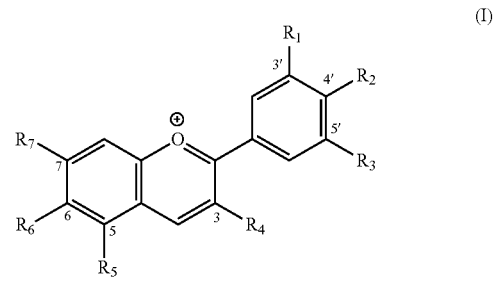

(I)

where each of $R_1$, $R_2$, $R_3$, $R_4$, $R_5$, $R_6$, and $R_7$ are, independently, —H, —OH, or —OCH$_3$, and wherein at least 15% of the anthocyanidins (e.g., at least or about 15%, 20%, 25%, 30%, 40%, 45%, 50%, or more of the anthocyanidins) are delphinidins. The anthocyanidin combinations rich in delphinidins can include both delphinidins and cyanidins While the compositions of the present invention are not limited to those in which a particular amount of the anthocyanidin is present, at least (or about) 35% of the compositions that comprise anthocyanidin combinations rich in delphinidins (e.g., at least or about 35, 40, 41, 42, 43, 44, 45 or 50% of the compositions that comprise anthocyanidin combinations rich in delphinidins) can be an anthocyanidin of Formula I.

Anthocyanins are water-soluble vacuolar flavonoid pigments that may appear red, purple or blue according to pH. Anthocyanins occur in tissues of higher plants and provide color in leaves, stems, roots, flowers and fruits. In photosynthetic tissues (such as leaves and some stems), anthocyanins protect cells from high-light damage by absorbing blue-green and UV light, thereby protecting the tissues from photoinhibition.

The anthocyanins (anthocyanidins with sugar group) are mostly 3-glucosides of the anthocyanidins. The anthocyanins are subdivided into the sugar-free anthocyanidin aglycones and the anthocyanin glycosides. We wish to make clear that the compositions that comprise anthocyanidin combinations rich in delphinidins can include a mixture of anthocyanidins. The combinations of anthocyanidins rich in delphinidins can also comprise cyanidins.

With respect to the source, the present compositions can include combinations of anthocyanidins that are extracted from a plant, optionally including the fruit or other edible plant product, of the genus *Aristotelia, Aronia, Enterpe, Glycine, Prunus, Ribes, Rubus, Sambucus, Vaccinium*, or *Zea*. Where the genus *Aristotelia* is used, the extract can be made from the plant *Aristotelia chilensis*. The fruit or other edible plant product can be an acai berry, a bilberry, a black currant, a black soybean, a blackberry, blue corn, a blueberry, a cherry, a chokeberry, a cranberry, an elderberry, a gooseberry, a maqui berry, purple corn, a raspberry, or a red currant. Plants of the *Vaccinium* species, such as blueberry, cranberry and bilberry, *Rubus* berries including black raspberry, red raspberry and blackberry, blackcurrant, cherry, eggplant peel. black rice, Concord grape and muscadine grape, red wine, red cabbage and violet petals are rich in anthocyanins and can be used as a source of the present extracts. While anthocyanins are less abundant in banana, asparagus, pea, fennel, pear and potato, the fruits of these plants may also be used in making the present compositions. High amounts of anthocyanins are found in the seed coat of black soybean (*Glycine max* L. Men.) (2000 mg/100 g) and in skins and pulp of black chokeberry (*Aronia melanocarpa* L.) (1480 mg/100 g), which are also useful in making the present compositions.

In *Aristotelia chilensis* the main components are derivatives of cyanidin and delphinidin in the form of diglycosides, which are commonly present in the fruits at a concentration between about 0.9 and 1.5%.

More generally, the combinations of anthocyanidins can be prepared from any plant material that includes anthocyanins, such as berries from one or more plants in the genus *Aristotelia* (e.g., *Aristotelia chilensis*) or *Vaccinium* (e.g., *Vaccinium augustifolium* or *corimbosum*).

The compositions can further include a carrier or excipient (e.g., an oil, including a plant or animal oil (e.g., fish oil)) and can be formulated for oral administration. There may be added advantages to formulating the extracts in oils rich in polyunsaturated ω-3 acids such as *Oenothera biennis* or *Linum usatissimum* oils or fish oil. Any of the present compositions may also contain adjuvants including preservative agents, wetting agents, emulsifying agents, and dispersing agents. The action of microorganisms may be inhibited by the inclusion of an antibacterial, antifungal, or antiviral agent (e.g., parabens, chlorobutanol, phenol, sorbic acid, and the like). It may also be desirable to include isotonic agents, for example, sugars, sodium chloride and the like. Suitable buffering agents include: acetic acid and a salt (1-2% w/v); citric acid and a salt (1-3% w/v); boric acid and a salt (0.5-2.5% w/v); and phosphoric acid and a salt (0.8-2% w/v). Suitable preservatives include benzalkonium chloride (0.003-0.03% w/v); chlorobutanol (0.3-0.9% w/v); parabens (0.01-0.25% w/v) and thimerosal (0.004-0.02% w/v).

For oral administration, the compositions (including those described immediately above or otherwise herein) can be formulated as a tablet, dragee, or capsule (e.g., a hard or soft gelatin capsule or a cellulose-based capsule).

Alternatively, any of the present compositions can be formulated as, or incorporated into, a food product. The form of the food product can vary greatly and includes any drink or beverage (i.e., a solution ingested in liquid form), cereal or cereal-type bar or "energy" bar. When formulated as a beverage, the present compositions can include a composition as described herein, a beverage component and a diluent. The beverage component can include components to enhance the efficacy of the beverage in providing benefits such as fighting infection, providing a desirable nutritional profile, and for providing enhanced organoleptic properties. The beverage component can be tea, a carbonated drink, or a nutritional drink. The beverage component can further include one or more bracers or flavanols, sugar or non-caloric sweeteners, vitamins, flavouring agents, coloring agents, preservatives, acidulants, or diluents (e.g., water). The extracts or active compounds therein may be dispersed, solubilized, or otherwise mixed into the beverage formulation of the instant invention.

The compositions comprising anthocyanidin combinations rich in delphinidin can be used to treat a subject who has a condition in which the immune system is undesirably suppressed. For example, a composition comprising an anthocyanidin combination rich in delphinidins can act as an immunostimulant in a subject whose immune system is depressed. Compositions that are generated from purified or synthesized compounds (e.g., mixtures of anthocyanidins) can also be used in these treatment methods. The compositions can be administered to a subject (e.g., a human) in an amount and for a time sufficient to promote immunostimulation in the subject.

The immune suppression can occur, for example, in subjects who have cancer or acquired immunodeficiency syndrome.

Our studies indicate that compositions rich in delphinidin are useful in maintaining immune function in a subject (e.g., a human), including subjects who do not have any overt condition that is compromising the immune system. These methods encompass administering to the subject a composition that comprises a combination of anthocyanins and is rich in delphinidin. The compositions are administered in an amount and for a time sufficient to maintain immune function in the subject. As these compositions are useful in maintaining immune function and therefore promoting or supporting a healthy condition, they can be administered in conjunction with a diet program and for an exercise-program. These and any other of the present compositions can also be taken with meals. Immunity decreases with age, and natural immune responses are adversely affected both as a person ages and in association with numerous conditions. These conditions include the use of immunosuppressant drugs, stress, and various diseases such as cancer, AIDS, hepatitis, and others. The compositions comprising anthocyanidin combinations rich in delphinidins, can be used in any circumstance where one wishes to counteract the natural decay of immunity. For example, they can be administered to a generally healthy person. The person may be of a certain age (e.g., a man over fifty years old or a peri- or post-menopausal woman).

The compositions comprising anthocyanidin combinations rich in delphinidins, can also be used to counteract the decrease in immunity that occurs as a side effect of immunosuppressant treatment or in association with cancer and infections (e.g., bacterial, fungal, or viral infections).

Lack of proper cellular immune (interferon gamma, some interleukins) response is a key feature that is implicated in a number of life-threatening disorders.

While the subject can be a human, the invention is not so limited. The compositions comprising anthocyanidin combinations rich in delphinidins can be administered to animals (e.g., animals kept as domestic pets, in zoos, or as livestock). In an animal kept as livestock (e.g., a cow, sheep, pig, goat, chicken, turkey, duck, or other bird), administration of the composition can obviate the need for prophylactic antibiotic treatment.

The compositions comprising anthocyanidin combinations rich in delphinidins can also be used to treat inflammation in a subject. For example, a composition comprising an anthocyanidin combination rich in delphinidins can be used to treat inflammation. Compositions that are generated from purified or synthesized compounds (e.g., mixtures of anthocyanidins) can also be used in these treatment methods. The compositions can be administered to a subject (e.g., a human) in an amount and for a time sufficient to inhibit inflammation in the subject.

As one of ordinary skill in the art would recognize, effective dosages can vary based on a number of parameters and particular dosages can be determined by methodologies known in the art. Generally, we expect therapeutically effective amounts of the present compositions or active ingredients therein to vary from about 0.001 mg/kg body weight to about 10 g/kg body weight (e.g., about 0.005, 0.01, 0.05, 0.1, 1.0, 10.0, 100, 250, or 500 mg/kg body weight). According to some such embodiments, the therapeutically effective amount of a composition comprising an anthocyanidin combination rich in delphinidins is at least or about 1 g/kg per body weight (e.g., at least or about 2.5, 5.0, 7.5, or 10.0 g/kg body weight). These dosages are pertinent regardless of the precise content or intended use.

The inflammation can be caused by a variety of conditions or an external injury. For example, the inflammation can be caused by a burn or other traumatic injury, a chemical irritant or toxin, an infection (e.g., a bacterial or viral infection), or an autoimmune disease.

The compositions that comprise a combination of anthocyanidins rich in delphinidins can be administered to a subject for the treatment of metabolic syndrome. The composition can be administered in an amount and for a time sufficient to improve a sign or symptom of the metabolic syndrome. With this method or any of the methods described herein, the method can include a step of identifying a subject who would be expected to benefit from the administration of a composition. For example, the present method can include a step of performing diagnostic tests and/or patient examinations and/or interviews to determine whether a patient has, or is likely to have, metabolic syndrome and would, therefore, be a candidate for treatment with the compositions just described. Metabolic syndrome is associated with obesity and diabetes. Accordingly, the compositions that comprise anthocyanidin combinations rich in delphinidin can be used to treat obesity and/or diabetes (e.g., type II diabetes) whether those conditions occur within the context of metabolic syndrome or independent of metabolic syndrome. The compositions that comprise anthocyanidin combinations rich in delphinidin can also be used to help regulate cholesterol levels, including the levels of LDL and triglycerides. Here too, the present compositions can be used to treat these conditions in the context of metabolic syndrome or independent of that syndrome.

The incidence of type II diabetes is rapidly increasing worldwide, and it has reached epidemic proportions in the western world. It is also increasing in developing countries, with an estimated 194 million people currently afflicted. Peripheral insulin resistance is a key feature, and this phenomenon is implicated in a number of life-threatening disorders collectively referred to as the metabolic syndrome (or Syndrome X).

In other embodiments, the compositions can comprise (a) anthocyanidin combinations rich in delphinidins, and (b) compositions that comprise andrographolides. Delphinidin-rich compositions can be made from purified or synthesized compounds. At least 35% (e.g., at least or about 35%, 40%, 45% or 50%) of the anthocyanidin combinations rich in delphinidins can be an anthocyanidin of the following formula:

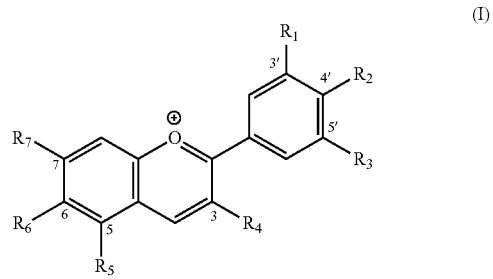

(I)

where each of $R_1$, $R_2$, $R_3$, $R_4$, $R_5$, $R_6$, and $R_7$ are, independently, —H, —OH, or —OCH$_3$, and wherein at least 15% of the anthocyanidins (e.g., at least or about 15%, 20%, 25%, 30%, 40%, 45%, 50%, or more of the anthocyanidins) are delphinidin. The anthocyanidin combinations rich in delphinidins can include both delphinidins and cyanidins, and the compounds can be extracted from a plant, optionally including the fruit or other edible plant product, of the genus *Aristotelia* (e.g., *Aristotelia chilensis*), *Aronia, Enterpe, Glycine, Prunus, Ribes, Rubus, Sambucus, Vaccinium*, or *Zea*.

The fruit or other edible plant product can be an acai berry, a bilberry, a black currant, a black soybean, a blackberry, blue corn, a blueberry, a cherry, a chokeberry, a cranberry, an elderberry, a gooseberry, a maqui berry, purple corn, a raspberry, or a red currant.

At least 30% of the compositions that comprise andrographolides (e.g., at least or about 30, 35, 40 or 45%) can be an andrographolide (e.g., an andrographolide, a deoxyandrographolide, a neoandrographolide, or a mixture thereof). The compositions that comprise andrographolides can be prepared from the herba (e.g., the leaves) of a plant of the genus *Andrographis* (e.g., *Andrographus paniculata*).

The ratio of the anthocyanidins combinations rich in delphinidins to the combinations that comprise andrographolides can be about 1.0:0.5 (w:w) to about 1.0:10.0 (w:w) (e.g., about 1.0:0.1, 1.0:0.5, 1.0:1.0, 1.0:1.5, 1.0:2.0, 1.0:2.5, 1.0:3.0, 1.0:3.5, 1.0:4.0, 1.0:4.5, 1.0:5.0, 1.0:5.5, 1.0:6.0, 1.0:6.5, 1.0:7.0, 1.0:7.5, 1.0:8.0, 1.0:8.5, 1.0:9.0, 1.0:9.5, 1.0:10.0, or 1.0:10.5).

Compositions comprising anthocyanidin combinations rich in delphinidins combined with compositions that comprise andrographolides can be formulated with a carrier or excipient and administered as a nutraceutical or in the context of a food product.

The compositions comprising anthocyanidin combinations rich in delphinidin combined with compositions that comprise andrographolides can be used to treat a subject who has a condition in which the immune system is undesirably suppressed. For example, a composition comprising an anthocyanidin combination rich in delphinidin combined with a composition that comprise an andrographolides combination can act as an immunostimulant in a subject whose immune system is depressed. Compositions that are generated from purified or synthesized compounds (e.g., mixtures of anthocyanidins and andrographolides) can also be used in these treatment methods. The compositions can be administered to a subject (e.g., a human) in an amount and for a time sufficient to promote immunostimulation in the subject.

The immune suppression can occur, for example, in subjects who have cancer or acquired immunodeficiency syndrome.

Our studies indicate that compositions comprising anthocyanidin combinations rich in delphinidins combined with compositions that comprise andrographolides are useful in maintaining immune function in a subject (e.g., a human), including subjects who do not have any overt condition that is compromising the immune system. These methods encompass administering to the subject a composition that includes compositions comprising a) anthocyanidin combinations rich in delphinidins, and b) compositions that comprise andrographolides The compositions are administered in an amount and for a time sufficient to maintain immune function in the subject. As these compositions are useful in maintaining immune function and therefore promoting or supporting a healthy condition, they (and other compositions described herein) can be administered in conjunction with a diet program and for an exercise-program. These and any other of the present compositions can also be taken with meals. Immunity decreases with age, and natural immune responses are adversely affected both as a person ages and in association with numerous conditions. These conditions include the use of immunosuppressant drugs, stress, and various diseases such as cancer, AIDS, hepatitis, and others. The compositions comprising anthocyanidin combinations rich in delphinidins combined with compositions that comprise andrographolides, can be used in any circumstance where one wishes to counteract the natural decay of immunity. For example, they can be administered to a generally healthy person. The person may be of a certain age (e.g., a man over fifty years old or a peri- or post-menopausal woman).

The compositions comprising anthocyanidin combinations rich in delphinidins combined with compositions that comprise andrographolides, can also be used to counteract the decrease in immunity that occurs as a side effect of immunosuppressant treatment or in association with cancer and infections (e.g., bacterial, fungal, or viral infections).

Lack of proper cellular immune (interferon gamma, some interleukins) response is a key feature that is implicated in a number of life-threatening disorders.

While the subject can be a human, the invention is not so limited. The compositions comprising anthocyanidin combinations rich in delphinidins combined with compositions that comprise andrographolides can be administered to animals (e.g., animals kept as domestic pets, in zoos, or as livestock). In an animal kept as livestock (e.g., a cow, sheep, pig, goat, chicken, turkey, duck, or other bird), administration of the composition can obviate the need for prophylactic antibiotic treatment.

The compositions comprising anthocyanidin combinations rich in delphinidins combined with compositions that comprise andrographolides can also be used to treat inflammation in a subject. For example, a composition comprising an anthocyanidin combination rich in delphinidins combined with a composition that comprises andrographolides can be used to treat inflammation. Compositions that are generated from purified or synthesized compounds (e.g., mixtures of anthocyanidins and andrographolides) can also be used in these treatment methods. The compositions can be administered to a subject (e.g., a human) in an amount and for a time sufficient to inhibit inflammation in the subject.

As one of ordinary skill in the art would recognize, effective dosages can vary based on a number of parameters and particular dosages can be determined by methodologies known in the art. Generally, we expect therapeutically effective amounts of the present compositions or active ingredients therein to vary from about 0.001 mg/kg body weight to about 10 g/kg body weight (e.g., about 0.005, 0.01, 0.05, 0.1, 1.0, 10.0, 100, 250, or 500 mg/kg body weight). According to some such embodiments, the therapeutically effective amount of a composition comprising an anthocyanidin combination rich in delphinidins combined with a composition that comprise andrographolides is at least or about 1 g/kg per body weight (e.g., at least or about 2.5, 5.0, 7.5, or 10.0 g/kg body, weight). These dosages are pertinent regardless of the precise content or intended use.

The inflammation can be caused by a variety of conditions or an external injury. For example, the inflammation can be caused by a burn or other traumatic injury, a chemical irritant or toxin, an infection (e.g., a bacterial or viral infection), or an autoimmune disease.

The compositions comprising anthocyanidin combinations rich in delphinidins combined with compositions that comprise andrographolides can be administered to a subject for the treatment of metabolic syndrome. The composition can be administered in an amount and for a time sufficient to improve a sign or symptom of the metabolic syndrome. With this method or any of the methods described herein, the method can include a step of identifying a subject who would be expected to benefit from the administration of a composition. For example, the present method can include a step of performing diagnostic tests and/or patient examinations and/or interviews to determine whether a patient has, or is likely to have, metabolic syndrome and would, therefore, be a candidate for treatment with the compositions just described. Metabolic syndrome is associated with obesity and diabetes. Accordingly, the compositions comprising anthocyanidin combinations rich in delphinidins combined with compositions that comprise andrographolides can be used to treat obesity and/or diabetes (e.g., type II diabetes) whether those conditions occur within the context of metabolic syndrome or independent of metabolic syndrome. The compositions comprising anthocyanidin combinations rich in delphinidins combined with compositions that comprise andrographolides can also be used to help regulate cholesterol levels, including the levels of LDL and triglycerides. Here too, the present compositions can be used to treat these conditions in the context of metabolic syndrome or independent of that syndrome.

The incidence of type II diabetes is rapidly increasing worldwide, and it has reached epidemic proportions in the western world. It is also increasing in developing countries, with an estimated 194 million people currently afflicted. Peripheral insulin resistance is a key feature, and this phenomenon is implicated in a number of life-threatening disorders collectively referred to as the metabolic syndrome (or Syndrome X). In other embodiments, the invention features compositions comprising (a) anthocyanidin combinations rich in delphinidins, and (b) compositions that comprise combinations of compounds selected from myrtillin, quercetin, or caffeoyl quinic derivatives and proanthocyanidins. In these compositions, at least or about 35% (e.g., at least or about 35%, 40%, 41%, 42%, 43%, 44%, 45%, or 50%) of the compositions comprising anthocyanidin combinations rich in delphinidins includes an anthocyanidin of the following formula:

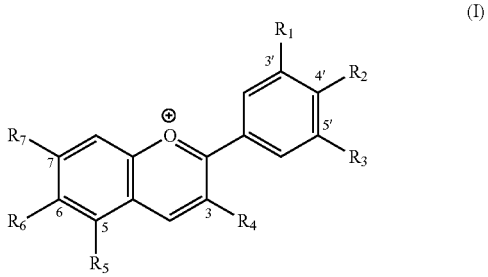

(I)

where each of $R_1$, $R_2$, $R_3$, $R_4$, $R_5$, $R_6$, and $R_7$ are, independently, —H, —OH, or —OCH$_3$, and wherein at least 15% of the anthocyanidins (e.g., at least or about 15%, 20%, 25%, 30%, 40%, 45%, 50%, or more of the anthocyanidins) are delphinidins. The anthocyanidin combination rich in delphinidin can include both delphinidin and cyanidin. The compositions comprising anthocyanidin combinations rich in delphinidins can be extracted from a plant of the genus *Aristotelia* that can be an *Aristotelia chilensis* plant, and the compositions that comprise combinations of compounds selected from myrtillin, quercetin, or caffeoyl quinic derivatives and proanthocyanidins can be extracted from a plant of the genus *Vaccinium* that can be, for example, *Vaccinium augustifolium* and/or *Vaccinium myrtillus* and/or *Vaccinium corimbosum*. Other species of *Vaccinium* can be used, but these are among the most economically viable sources.

In one embodiment the compositions that comprise combinations of compounds selected from myrtillin, quercetin, or caffeoyl quinic derivatives and proanthocyanidins can be extracted from the herba (the leaves) of a plant of the genus *Vaccinium*.

The compositions from a plant of the genus *Vaccinium* can include myrtillin, quercetin, or a caffeic acid derivative (e.g., chlorogenic acid). In extracts of *Vaccinium augustifolium* and/or *corimbosum*, the content of caffeoylquinic acid can be in the range of 20%.

The ratio of the compositions that comprise anthocyanidin combinations rich in delphinidins to the compositions that comprise combinations of compounds selected from myrtillin, quercetin, or caffeoyl quinic derivatives and proanthocyanidins can be about 1.0:0.5 (w:w) to about 1.0:10.0 (w:w). For example, the ratio can be about 1.0:0.1, 1.0:0.5, 1.0:1.0, 1.0:1.5, 1.0:2.0, 1.0:2.5, 1.0:3.0, 1.0:3.5, 1.0:4.0, 1.0:4.5, 1.0:5.0, 1.0:5.5, 1.0:6.0, 1.0:6.5, 1.0:7.0, 1.0:7.5, 1.0:8.0, 1.0:8.5, 1.0:9.0, 1.0:9.5. 1.0:10.0, or 1.0:10.5. As with other compositions described herein, these compositions can be prepared from purified or synthesized compounds (e.g., from anthocyanidins and myrtillin, quercetin, or a caffeic acid derivative) rather than extracted from the plant materials per se.

Regardless of the source of the ingredients, the compounds can be formulated for oral administration or consumption. For example, the compositions can further include a carrier or an excipient (e.g., a vegetable oil or animal oil (e.g., fish oil)). The compositions can be fashioned using known techniques into tablets, capsules, and the like, for oral administration or incorporated into a food product (e.g., a drink (or beverage) or cereal-type bar).

The compositions including (a) anthocyanidin combinations rich in delphinidins, and (b) compositions that comprise combinations of compounds selected from myrtillin, quercetin, or caffeoyl quinic derivatives and proanthocyanidins can be administered to a subject for the treatment of metabolic syndrome. The composition can be administered in an amount and for a time sufficient to improve a sign or symptom of the metabolic syndrome. With this method or any of the methods described herein, the method can include a step of identifying a subject who would be expected to benefit from the administration of a composition. For example, the present method can include a step of performing diagnostic tests and/or patient examinations and/or interviews to determine whether a patient has, or is likely to have, metabolic syndrome and would, therefore, be a candidate for treatment with the compositions just described. Metabolic syndrome is associated with obesity and diabetes. Accordingly, the compositions that comprise combinations of compounds selected from myrtillin, quercetin, or caffeoyl quinic derivatives and proanthocyanidins can be extracted from a plant of the genus *Vaccinium* can be used to treat obesity and/or diabetes (e.g., type II diabetes) whether those conditions occur within the context of metabolic syndrome or independent of metabolic syndrome. The compositions that comprise combinations of compounds selected from myrtillin, quercetin, or caffeoyl quinic derivatives and proanthocyanidins can be extracted from a plant of the genus *Vaccinium* can also be used to help regulate cholesterol levels, including the levels of LDL and triglycerides. Here too, the present compositions can be used to treat these conditions in the context of metabolic syndrome or independent of that syndrome.

The incidence of type II diabetes is rapidly increasing worldwide, and it has reached epidemic proportions in the western world. It is also increasing in developing Countries, with an estimated 194 million people currently afflicted. Peripheral insulin resistance is a key feature, and this phenomenon is implicated in a number of life-threatening disorders collectively referred to as the metabolic syndrome (or Syndrome X).

While we often refer to anthocyanidins, the sugar-containing counterparts of anthocyanidins (the anthocyanoside flavenoids or anthocyanins) can also be included in the present compositions. The amounts referred to below are thus applicable to anthocyanidins, anthocyanosides, or a combination of the two (either or both of which may be included in the present compositions). Thus, in any embodiment, the compositions can include one or more compounds that are sugar-containing counterparts of an anthocyanidin. That is, the compositions can include, in addition to, or in place of, one or more of the anthocyanidins recited herein, a corresponding sugar-containing anthocyanoside flavenoid (also known as an anthocyanin). Accordingly, the compositions comprising anthocyanidin combinations can include at least one of delphinidin-3-galactoside; delphinidin-3-glucoside; cyanidin-3-galactoside; delphinidin-3-arabinoside; cyanidin-3-glucoside; petunidin-3-galactoside; petunidin-3-glucoside; cyanidin-3-arabinoside; peonidin-3-galactoside; perunidin-3-arabinoside; malvidin-3-galactoside; peonidin-3-glucoside; malvidin-3-glucoside; peonidin-3-arabinoside; malvidin-3-arabinoside; delphinidin-6-acetyl-3-glucoside; cyanidin-6-acetyl-3-glucoside; malvidin-6-acetyl-3-galactoside; petunidin-6-acetyl-3-glucoside; peonidin-6-acetyl-3-glucoside; and malvidin-6-acetyl-3-glucoside. Alternatively, or in addition, the extracts can include at least one of delphinidin 3-sambubioside-5-glucoside; delphinidin 3,5-diglucoside; cyanidin 3-sambubioside-5-glucoside; cyanidin 3,5-diglucoside; delphinidin 3-sambubioside; delphinidin 3-glucoside; cyanidin 3-sambubioside; and cyanidin 3-glucoside.

TABLE 1

Selected anthocyanidins and their substitutions.

| Anthocyanidin | $R_1$ | $R_2$ | $R_3$ | $R_4$ | $R_5$ | $R_6$ | $R_7$ |
| --- | --- | --- | --- | --- | --- | --- | --- |
| Aurantinidin | —H | —OH | —H | —OH | —OH | —OH | —OH |
| Cyanidin | —OH | —OH | —H | —OH | —OH | —H | —OH |
| Delphinidin | —OH | —OH | —OH | —OH | —OH | —H | —OH |
| Eupopinidin | —OCH$_3$ | —OH | —OH | —OH | —OCH$_3$ | —H | —OH |
| Luteolinidin | —OH | —OH | —H | —H | —OH | —H | —OH |
| Pelargonidin | —H | —OH | —H | —OH | —OH | —H | —OH |
| Malvidin | —OCH$_3$ | —OH | —OCH$_3$ | —OH | —OH | —H | —OH |
| Peonidin | —OCH$_3$ | —OH | —H | —OH | —OH | —H | —OH |
| Petunidin | —OH | —OH | —OCH$_3$ | —OH | —OH | —H | —OH |
| Rosinidin | —OCH$_3$ | —OH | —H | —OH | —OH | —H | —OCH$_3$ |

Table 1 shows selected anthocyanidins of formula 1 and their substitutions, any of which can be incorporated into the compositions of the present invention as specified. As noted, an aglycolic counterpart may also be used.

The compositions can be aqueous compositions.

To improve oral absorption, the present compositions can be suspended in lipophilic carriers, which can include vegetable oils (e.g., peanut oil, soybean oil, corn oil, and olive oil) semisynthetic vegetable oils, such as fractionated coconut oil (a medium chain fatty acid triglyceride mixture), unsaturated polyglycolysed glycerides (GPGI) and mineral oil, such as liquid paraffin. Animal oils, including fish oils, can also be used. Regardless of the precise source, the oils can also be those that are rich in unsaturated omega-3 fatty acids and phospholipids.

Suspensions can be prepared by suspending micronized extracts in the carrier (e.g., by stirring at room temperature). Conventional rheological modifiers can also be added to optimize the physical stability of the suspensions, as well as conventional surfactants (which we may refer to more generally as a carrier or excipient), such as soybean lecithin, to ensure a good wettability. The resulting oily suspensions can then be directly distributed in gelatine capsules or absorbed on suitable excipients, such as colloidal silicon dioxide, starch or mannitol. In the second instance, kneads can be obtained that are granulated and distributed in sachets or used for preparing tablets.

Other polyphenols and triterpenes with oleanane and ursane skeletons may be present in the compositions of the present invention and will also improve their effects.

With respect to the amounts of anthocyanidins or anthocyanosides, the upper limit can be no more than 50%, 60%, 70%, 75%, 80%, 85%. or 90%. For example, in a composition, the anthocyanidin content can be at least 5% (e.g., 30%) but less than 80% of the extract (w/w).

Our studies to date indicate that the compositions described herein work synergistically. Thus, the compositions comprising anthocyanidin combinations combined with the compositions comprising andrographolides or with the compositions that comprise combinations of compounds selected from myrtillin, quercetin, or caffeoyl quinic derivatives and proanthocyanidins an effect that is greater than one would expect from simply combining the two compositions; they are not simply additive.

The compositions described herein may also include some diterpenes. As these compounds have immunostimulatory effects, they may be included in any of the present compositions.

In one embodiment, the compositions can be extracted from the aforementioned plants.

The extracts of the selected plants can be prepared according to processes that are known and used in the art to prepare botanical extracts. The processes can be standardized to improve reproducibility and consistency from extract to extract. The processes can begin with ripe fruits, fresh or frozen, or, where specified, the herba of a plant. Extraction can proceed in ethanol in the presence of organic or mineral acids or by extracting the fruits with water in the presence of bisulfite ions. See J. B. Hrborne, The flavonoids, Chapman & Hall Ed. London p 227. The bisulfite ions may be prepared by methods known in the art (e.g., by the addition of sulfur dioxide or simply by addition of sodium methabisulfite).

The ratio between the fruits and water containing methabisulfite is 1:10 and the ratio between anthocyanosides and sodium bisulfite in molarity is 1:3. The solution of bisulfite adducts, whose pH generally ranges from 1 to 3.5 can then be alkalinized until the pH reaches 5 and subsequently eluted through a column containing non-ionogenic polymeric resins. While in acidic conditions, the anthocyanoside-bisulfite adducts can be absorbed with other polyphenols present in the extract at pH 5. The bisulfite adducts remain surprisingly in solution whereas the other phenolics are absorbed and so separated from the anthocyanosides. With this procedure it is possible to prepare two extracts containing essentially all of the polyphenolic substances or the pure anthocyanoside family. In the case of the total phenolic fraction, the extract may not be alkanized and passed directly on the resin at acid pH; after absorption of the compounds the column can be eluted with water in order to eliminate salts and sugar and inert compounds. Finally, the resin is washed with ethanol for the recovery of the polyphenolic substances including the anthocyanosides as bisulfite adducts. The alcoholic solution can be concentrated under vacuum at a temperature ranging between about 25 and 40° C. (e.g., 35° C.) until half of the volume of the weight fruits is achieved. The concentrate can then be acidified with diluted acid (e.g., hydrochloric acid) under stirring in a nitrogen-rich atmosphere to remove sulphur dioxide. The gas flow can be bubbled in a sodium hydroxide aqueous solution to avoid sulphur dioxide pollution in the environment. The concentrate containing all of the phenolic substances could be evaporated to dryness. In the case of the preparation of pure anthocyanoside fractions, the concentrate can be alkalinized at pH 6 and extracted with n-butanol or ethyl acetate to remove the procyanidins and tannin-like substances. The solution can then be acidified with hydrochloric acid to remove sulphur dioxide as described above. The anthocyanoside content in the extract in this case is in the range of 90-95%.

As far as the preparation of an andrographolide is concerned (e.g., the *Andrographis paniculata* extract), the dried leaves can be extracted after grinding with a mixture of water miscible alcohols (e.g., ethanol with water, such as ethanol/water 50% v/v) until the extractable substances are fully recovered. The combined hydro-alcoholic extracts are concentrated to water filtering at this point cloudy precipitates and fine particles of leaves etc. The resin can be eluted with water to largely eliminate undesired substances like sugars, peptides, and salts, and the active principle can then be eluted with ethanol 95% until the exhaustion or the same. The ethanolic eluate can be concentrated under vacuum at a temperature not to exceed about 40° C. The content of andrographolide would be expected to be in the range of 30 and 40% depending on certain factors such as the original content in the leaves.

This extract could be used as it is or in combination with the purified extract of *Aristotelis chilensis* or another anthocyanidin-containing plant.

The anthocyanins are subdivided into the sugar-free anthocyanidin aglycones and the anthocyanin glycosides, and the compositions of the present methods can include either or both of types of anthocyanins.

The therapeutically effective amount of an individual anthocyanin or of a particular anthocyanin or other active compound in the present compositions can vary from about 0.01 mg/kg body weight to about 1 g/kg body weight.

The anthocyanin component of the present compositions can include one or more of delphinidin-3-galactoside; delphindin-3-glucoside; cyanidin-3-galactoside; delphinidin-3-arabinoside; cyanidin-3-glucoside; petunidin-3-galactoside; petunidin-3-glucoside; cyanidin-3-arabinoside; peonidin-3-galactoside; perunidin-3-arabinoside; malvidin-3-galactoside; peonidin-3-glucoside; malvidin-3-glucoside; peonidin-3-arabinoside; malvidin-3-arabinoside; delphinidin-6-acetyl-3-glucoside; cyanidin-6-acetyl-3-glucoside; malvidin-6-acetyl-3-galactoside; petunidin-6-acetyl-3-glucoside; peonidin-6-acetyl-3-glucoside; malvidin-6-acetyl-3-glucoside; delphinidin 3-sambubioside-5-glucoside; delphinidin 3,5-diglucoside; cyanidin 3-sambubioside-5-glucoside; cyanidin 3,5-diglucoside; delphinidin 3-sambubioside; delphinidin 3-glucoside; cyanidin 3-sambubioside; and cyanidin 3-glucoside.

We may use the terms "therapeutic agent" and "active agent" interchangeably to refer to the compound(s) in the present compositions that interact in some way with a subject or patient's body to elicit a desired physiological response or outcome. The active agent may be, for example, but is not limited to, at least one of a flavonoid or an anthocyanin, or a derivative or variant thereof, an anthocyanin of blueberry such as, for example, delphinidin-3-galactoside; delphindin-3-glucoside; cyanidin-3-galactoside; delphinidin-3-arabinoside; cyanidin-3-glucoside; petunidin-3-galactoside; petunidin-3-glucoside; cyanidin-3-arabinoside; peonidin-3-galactoside; perunidin-3-arabinoside; malvidin-3-galactoside; peonidin-3-glucoside; malvidin-3-glucoside; peonidin-3-arabinoside; malvidin-3-arabinoside; delphinidin-6-acetyl-3-glucoside; cyanidin-6-acetyl-3-glucoside; malvidin-6-acetyl-3-galactoside; petunidin-6-acetyl-3-glucoside; peonidin-6-acetyl-3-glucoside; malvidin-6-acetyl-3-glucoside, or an anthocyanin of maqui berries such as, for example, delphinidin 3-sambubioside-5-glucoside; delphinidin 3,5-diglucoside; cyanidin 3-sambubioside-5-glucoside; cyanidin 3,5-diglucoside; delphinidin 3-sambubioside; delphinidin 3-glucoside; cyanidin 3-sambubioside; cyanidin 3-glucoside, and combinations thereof.

"Extracting" as used herein refers to the process of drawing out, withdrawing, distilling or otherwise separating one substance from another by a chemical or physical process. The extract can be a solid, viscid, or liquid substance extracted from a plant or, for example, a mixed population of synthetic compounds, or the like, containing its essence in concentrated form. We may also refer to a "carrier" as a "drug carrier", "carrier", or "vehicle," and these terms refer to carrier materials suitable for administration of the anthocyanin compounds as described herein, or variants or derivatives thereof. Carriers useful in the present compositions include many materials known in the art that are nontoxic and do not actively interact with other components (i.e., they are considered inert). A "pharmaceutically acceptable carrier" is any substantially non-toxic carrier conventionally used in pharmaceuticals that may improve the stability or bioavailability of the active agent. Useful carriers include esterified glycerides, which may be saturated or unsaturated. Useful carriers also include polyethylene glycol and fatty acids. The pharmaceutical compositions of the invention can also include suitable solid or gel phase carriers or excipients (e.g., calcium carbonate, calcium phosphate, various sugars, starches, cellulose derivatives, gelatin, and polymers such as polyethylene glycol, as mentioned above).

Whether liquid or solid, the present pharmaceutical compositions can be microencapsulated, and if appropriate, with one or more excipients, encochleated, coated onto microscopic gold particles, contained in liposomes, pellets for implantation into the tissue, or dried onto an object to be rubbed into the tissue. The present pharmaceutical compositions also may be in the form of granules, beads, powders, tablets, coated tablets, (micro)capsules, suppositories, syrups, emulsions, suspensions, creams, drops or preparations with protracted release of active compounds, in whose preparation excipients and additives and/or auxiliaries such as disintegrants, binders, coating agents, swelling agents, lubricants, or solubilizers are customarily used as described above. The pharmaceutical compositions are suitable for use in a variety of drug delivery systems.

The anthocyans described herein may be delivered in the form of a pharmaceutically acceptable salt. When used in medicine, the salts should be pharmaceutically acceptable, but non-pharmaceutically acceptable salts may conveniently be used to prepare pharmaceutically acceptable salts thereof. Such salts include, but are not limited to, those prepared from the following acids: hydrochloric, hydrobromic, sulphuric, nitric, phosphoric, maleic, acetic, salicylic, p-toluene sulphonic, tartaric, citric, methane sulphonic, formic, malonic, succinic, naphthalene-2-sulphonic, and benzene sulphonic. Also, such salts may be prepared as alkaline metal or alkaline earth salts, such as sodium, potassium or calcium salts of the carboxylic acid group. By "pharmaceutically acceptable salt" is meant those salts which are, within the scope of sound medical judgment, suitable for use in contact with the tissues of humans and lower animals without undue toxicity, irritation, allergic response and the like and are commensurate with a reasonable benefit/risk ratio. The salts may be prepared in situ during the final isolation and purification of the compounds described within the present invention or separately by reacting a free base function with a suitable organic acid. Representative acid addition salts include, but are not limited to, acetate, adipate, alginate, citrate, aspartate, benzoate, benzenesulfonate, bisulfate, butyrate, camphorate, camphorsulfonate, digluconate, glycerophosphate, hemisulfate, heptanoate, hexanoate, fumarate, hydrochloride, hydrobromide, hydroiodide, 2-hydroxyethansulfonate(isethionate), lactate, maleate, methanesulfonate, nicotinate, 2-naphthalenesulfonate, oxalate, pamoate, pectinate, persulfate, 3-phenylpropionate, picrate, pivalate, propionate, succinate, tartrate, thiocyanate, phosphate, glutamate, bicarbonate, p-toluenesulfonate and undecanoate. Also, the basic nitrogen-containing groups may be quaternized with such agents as lower alkyl halides such as methyl, ethyl, propyl, and butyl chlorides, bromides and iodides; dialkyl sulfates like dimethyl, diethyl, dibutyl and diamyl sulfates; long chain halides such as decyl, lauryl, myristyl and stearyl chlorides, bromides and iodides; arylalkyl halides like benzyl and phenethyl bromides and others. Water or oil-soluble or dispersible products are thereby obtained. Examples of acids which may be employed to form pharmaceutically acceptable acid addition salts include such inorganic acids as hydrochloric acid, hydrobromic acid, sulphuric acid and phosphoric acid and such organic acids as oxalic acid, maleic acid, succinic acid and citric acid. Basic addition salts may be prepared in situ during the final isolation and purification of compounds described within the invention by reacting a carboxylic acid-containing moiety with a suitable base such as the hydroxide, carbonate or bicarbonate of a pharmaceutically acceptable metal cation or with ammonia or an organic primary, secondary or tertiary amine. Pharmaceutically acceptable salts include, but are not limited to, cations based on alkali metals or alkaline earth metals such as lithium, sodium, potassium, calcium, magnesium and aluminum salts and the like and nontoxic quaternary ammonia and amine cations including ammonium, tetramethylammonium, tetraethylammonium, methylamine, dimethylamine, trimethylamine, triethylamine, diethylamine, ethylamine and the like. Other representative organic amines useful for the formation of base addition salts include ethylenediamine, ethanolamine, diethanolamine, piperidine, piperazine and the like. Pharmaceutically acceptable salts may be also obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium or magnesium) salts of carboxylic acids may also be made.

The formulations may be presented conveniently in unit dosage form and may be prepared by any of the methods well known in the art of pharmacy. All methods include the step of bringing into association a sugar-free anthocyanidin aglycone and/or an anthocyanin glycoside, or a derivative or variant thereof, with the carrier that constitutes one or more accessory agents. In general, the formulations are prepared by uniformly and intimately bringing into association the active agent with liquid carriers or finely divided solid carriers or both and then, if necessary, shaping the product into the desired formulation.

The anthocyanins and anthocyanidins as described herein, or a pharmaceutically acceptable ester, salt, solvate or prodrug thereof may be mixed with other active materials that do not impair the desired action, or with materials that supplement the desired action (e.g., the andrographolides described herein). Solutions or suspensions used for parenteral, intradermal, subcutaneous, intrathecal, or topical application may include, but are not limited to, for example, the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parental preparation may be enclosed in ampoules, disposable syringes or multiple dose vials made of glass or plastic. Administered intravenously, particular carriers are physiological saline or phosphate buffered saline (PBS).

The following examples illustrate the invention in detail, but they are not intended to limit the scope of the invention. Other embodiments will be apparent to one of ordinary skill in the art.

EXAMPLES

Example 1: Preparation of *A. chilensis* Extract Containing Anthocyanidins and Polyphenols Frozen fruits of *Aristotelia chilensis* (1 kg) containing 15 g of anthocyanidins were extracted with 5×1 L of ethanol/water, 50% v/v; each extraction was carried out for 4 hours. For both the first and second extractions, 7.5 g of sodium bisulfite were dissolved in the ethanol/water solvent. The extracted liquids were concentrated under vacuum at a temperature of 30° C. to a volume of 2 L in order to eliminate the ethanol. The concentrate was loaded on to a column of 2.5 L of a non-polar polystyrenic resin having a particle size of 25-60 mesh. The column was washed with 10 L of water and then washed with 3 L of ethanol (95%). The ethanolic solution was concentrated to 0.5 L (essentially removing the ethanol) with stirring, and the concentrated solution was acidified to pH 1 in a current of nitrogen to remove the $SO_2$, by bubbling into an NaOH solution. The dark red solution was then carefully concentrated under vacuum to dryness. 150 g of extract was obtained with an anthocyanidin content of about 30%.

Example 2: Preparation of *A. chilensis* Extract Containing Anthocyanidins and Polyphenols An *Aristotelia chilensis* extract containing both anthocyanidins and polyphenols was prepared essentially according to the method in Example 1, except that the ethanolic solution was concentrated to 1 L and, after acidification, was diluted to 2.5 L with water and loaded onto a 2 L polystyrene column as described in Example 1. The column was eluted with ethanol as described. With this process, the yield of the extract was about 135 grams and included about 41% anthocyanidins.

Example 3: Preparing an Extract with High Content of Anthocyanidins from *A. chilensis*

Frozen fruits of *Aristotelia chilensis* (1 kg) containing 15 g of anthocyanidins were extracted with 5×1 L of ethanol/water 50% v/v. Each extraction was carried out for 4 hours. For both the first and second extractions, 7.5 g of sodium bisulfite were dissolved in the ethanol/water solvent. The extracted liquids were concentrated under vacuum at a temperature of 30° C. to a volume of 2 L in order to eliminate the ethanol. The mixture was alkalinized to pH 5.5 by addition of a 10% solution of NaOH and loaded on a column containing 2 L of non-polar polystyrenic resins. The column was eluted with 2 L of water. The aqueous eluate was then concentrated to 2 L and acidified to pH 1 by addition of hydrochloric acid and then loaded on another 2 L column of a non-polar polystyrenic resin. We continued washing with water until the eluate was colourless. Anthocyanidins were recovered from the resin by washing with ethanol until the ethanol was colourless. The alcoholic solution was concentrated to dryness, yielding 50 g of an extract containing 95% anthocyanidins.

Example 4: Preparation of an Extract with a High Content of Andrographolides

Dried leaves of *Andrographis paniculata* (1 kg) were extracted with 5 L of ethanol/water 50% v/v for 4 hours at 60° C. Three additional extractions were performed using 3 L of the same mixture of solvent, and the combined extracts were concentrated under vacuum at a temperature of 45° C. until the alcohol was eliminated. The aqueous extract was centrifuged to eliminate polymeric flocculates and turbidity and the clear solution was passed through 3 L of a non-polar polystyrenic resin. The column was eluted with 2 L of water. The absorbed material was recovered by ethanol washing of the resin until alcoholic eluates were colourless. The alcoholic solution was concentrated to dryness, yielding 120 g of an extract containing about 35% of total andrographolides (10% of andrographolide, 3% deoxyandrographolide and 1% of neoandrographolide).

Example 5: An Extract with a High Content in Caffeoyl Esters of Quinic Acid and Proanthocyanidins Dried leaves of *Vaccinium angustifolium* (1 kg) were extracted with 5 L of ethanol/water 50% v/v for 4 hours at 60° C. Three additional extractions were performed using 3 L of the same mixture of solvent, and the combined extracts were concentrated under vacuum at a temperature of 45° C. until the alcohol was eliminated. The aqueous extract was centrifuged to eliminate polymeric flocculates and turbidity and then the clear solution was passed through 3 L of a non-polar polystyrenic resin. The column was eluted with 2 L of water. The absorbed material was recovered by ethanol washing the resin until the alcoholic eluates were colourless. The alcoholic solution was concentrated to dryness, yielding 120 g of an extract containing about 35% of caffeoyl quinic derivatives, 10% of procyanidins and 3% of triterpenic acids.

Example 6: Delphinidin Induced Intracellular Calcium Release in a Dose-Dependent Manner We evaluated the effect of delphinidin on intracellular calcium release in Jurkat T cells. Extracts were prepared according to the method of Example 1.

Jurkat T cells in Hanks' Balanced Salt Solution (HBSS) medium (Invitrogen) with 0.9 mM of $CaCl_2$ were loaded with Fura-2-acetoxymethyl ester (2.5 uM FURA 2-AM) for 30 min at 37° C., washed and incubated in 10 μM, 50 μM, and 100 μM delphinidin. The fluxes of $Ca^{2+}$ were measured as ratio of excitation at 340 and 380 nm, and emission at 509 nm, for 300 seconds, at 37° C. in a spectrofluorimeter (LS55, PerkinElmer).

TABLE 2

Fluxes of $Ca^{2+}$ induced by different concentrations of delphinidin.

| Concentration of delphinidin in the sample [μM] | Average area under the curve of ratio 340/380 during 300 seconds | Percentage compared to control [%] |
|---|---|---|
| 0 | 60 | 100 |
| 10 | 100 | 166.7 |

TABLE 2-continued

Fluxes of $Ca^{2+}$ induced by different concentrations of delphinidin.

| Concentration of delphinidin in the sample [μM] | Average area under the curve of ratio 340/380 during 300 seconds | Percentage compared to control [%] |
|---|---|---|
| 50 | 225 | 375 |
| 100 | 250 | 416.7 |

As shown in Table 2, the area under the curve (AUC) of the ratio of excitation of 340 to 380 nm, and emission at 509 nm during 300 seconds after treatments varied with the delphinidin concentration. For cells incubated in 10 μM, 50 μM, and 100 μM delphinidin, the area under the curve was 66.7%, 275% and 316.7% higher, respectively, than that obtained for untreated control cells. These results showed that delphinidin induced $Ca^{2+}$ fluxes in Jurkat T cells in a dose-dependent manner.

Example 7: Delphinidin Activated T Cells Via Calcium Fluxes

We next explored the mechanism of the effect of delphinidin on intracellular calcium entry and release in Jurkat T cells.

To measure calcium release, $4 \times 10^6$ FURA 2-AM-loaded Jurkat T cells were incubated in HBSS calcium free medium as decribed in Example 6. The cells were incubated in 50 uM delphinidin, or in 50 uM delphinidin and 10 μM N-[4-[3,5-bis(trifluoromethyl)-1H-pyrazol-1-yl]phenyl]-4-methyl-1,2,3-thiadiazole-5-carboxamide (BTP-2, a Store-Operated Calcium Entry (SOCE) inhibitor). The release of $Ca^{2+}$ was measured as ratio of excitation at 340 and 380 nm, and emission at 509 nm, for 200 seconds, at 37° C., in a spectrofluorimeter (LS55, PerkinElmer).

TABLE 3

Calcium release in samples of Jurkat T cells with different treatments.

| Treatment | Average AUC of ratio 340/380 during 200 seconds | Percentage compared to the control [%] |
|---|---|---|
| untreated | 3 | 100 |
| 50 μM delphinidin | 51 | 1700 |
| 50 μM delphinidin + 10 μM BTP-2 | 47 | 1566.7 |

As shown in Table 3, both the samples treated with delphinidin alone and the samples treated with delphinidin plus 10 uM BTP-2 generated a peak of the excitation ratio at 340 and 380 nm, and emission at 509 nm. The area under the curve (AUC) for the samples incubated in delphinidin alone and in dephinidin plus 10 uM BTP-2 was 1700% and 1566% higher, respectively, than that of the untreated control cells. These data suggested that both delphinidin alone and dephinidin plus 10 uM BTP-2 induced calcium release.

To measure calcium entry after 200 seconds, when the levels of calcium returned to the baseline, 0.9 mM of $CaCl_2$ was added, and the fluxes of $Ca^{2+}$ were measured as ratio of excitation ratio at 340 and 380 nm, and emission at 509 nm in a spectrofluorimeter during 150 seconds.

TABLE 4

Calcium entry in samples of Jurkat T cells with different treatments.

| Treatment | Average AUC of ratio 340/380 150 sec. after calcium treatments | Percentage compared to control [%] |
|---|---|---|
| Control samples | 38 | 100 |
| 50 μM delphinidin | 70 | 184.2 |
| 50 μM delphinidin + 10 μM BTP-2 | 38 | 100 |

As shown in Table 4, the area under the curve for the samples incubated in delphinidin alone and with dephinidin plus 10 uM BTP-2 was 184.2% and 100%, respectively, of the value obtained for the untreated control cells.

These results showed that BTP-2, an inhibitor of SOCE, inhibited the entry, but not the release of $CaCl_2$, suggesting that delphinidin induced intracellular calcium release and calcium entry via SOCE in Jurkat T cells and that delphinidin activated T cells via calcium fluxes.

Example 8: Delphinidin Induced Cellular Activation Characterized by Calcium Release in T Cells that is Reversible $4 \times 10^6$ FURA 2-AM-loaded Jurkat T cells were incubated in HBSS calcium free medium. The cells were then incubated in 50 uM delphinidin and the fluxes of $Ca^{2+}$ were measured as ratio of excitation at 340 and 380 nm, and emission at 509 nm, at 37° C. in a spectrofluorimeter (LS55, PerkinElmer).

As shown in FIG. 1, a peak of calcium release was observed following the delphinidin treatment. The peak gradually decreased to baseline after two minutes. These results showed that delphinidin induced reversible calcium release, suggesting that dephinidin activation of T cells was characterized by reversible calcium release.

Example 9: Delphinidin Induced Cellular Activation Via Store Operated Calcium Influx We evaluated the effect of delphinidin on store operated calcium influx essentially according to the method described in Example 7.

$4 \times 10^6$ FURA 2-AM-loaded Jurkat T cells were incubated in HBSS calcium free medium. The cells were incubated in 50 uM delphinidin or 50 uM delphinidin plus 10 μM BTP-2 and the fluxes of $Ca^{2+}$ were measured as ratio of excitation at 340 and 380 nm, and emission at 509 nm, at 37° C. in a spectrofluorimeter (LS55, PerkinElmer).

Figure 2:
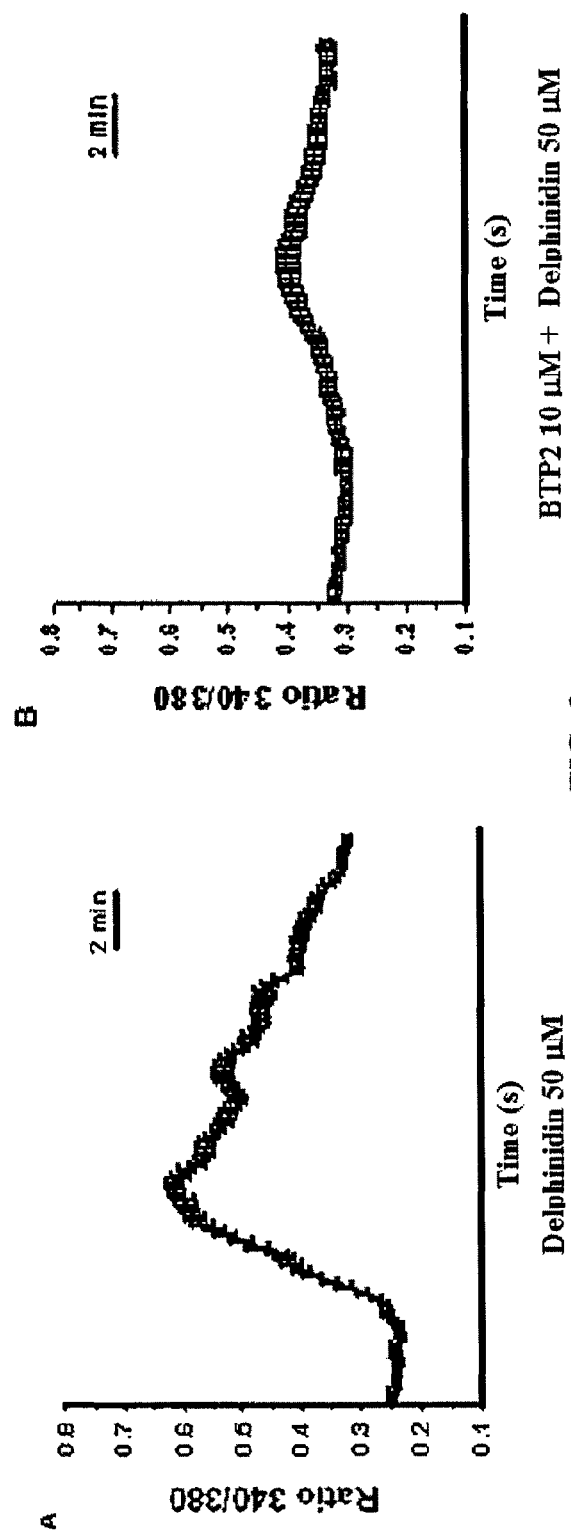
FIG. 2A shows the spectrofluorescence results for the average of 4 measurements of calcium fluxes in Jurkat T cells treated with the composition comprising delphinidin 50 µM.
FIG. 2B shows the spectrofluorescence results for the average of 4 measurements of calcium fluxes in Jurkat T cells treated with the composition comprising delphinidin 50 µM and BTP-2 10 µM.

FIG. 2A shows the spectrofluorescence results for the average of 4 measurements of calcium fluxes in Jurkat T cells incubated in delphinidin 50 μM. FIG. 2B shows the spectrofluorescence results for the average of 4 measurements of calcium fluxes in Jurkat T cells incubated in delphinidin 50 μM plus BTP-2 10 μM.

The delphinidin-induced calcium influx, shown in FIG. 2A, was reduced in the presence (FIG. 2B) of the Store-Operated Calcium Entry (SOCE) inhibitor, BTP-2. These results suggested that store-operated calcium channels were mediating delphinidin-induced calcium flux and that delphinidin induced cellular activation of Jurkat T cells via store operated calcium influx.

Example 10: Delphinidin Activated T Cell Calcium Release Via a PLC-Dependent Mechanism We evaluated the role of phospholipase C (PLC) in delphinidin induced calcium release using the selective phospholipase C inhibitor, U73122.

Figure 3:
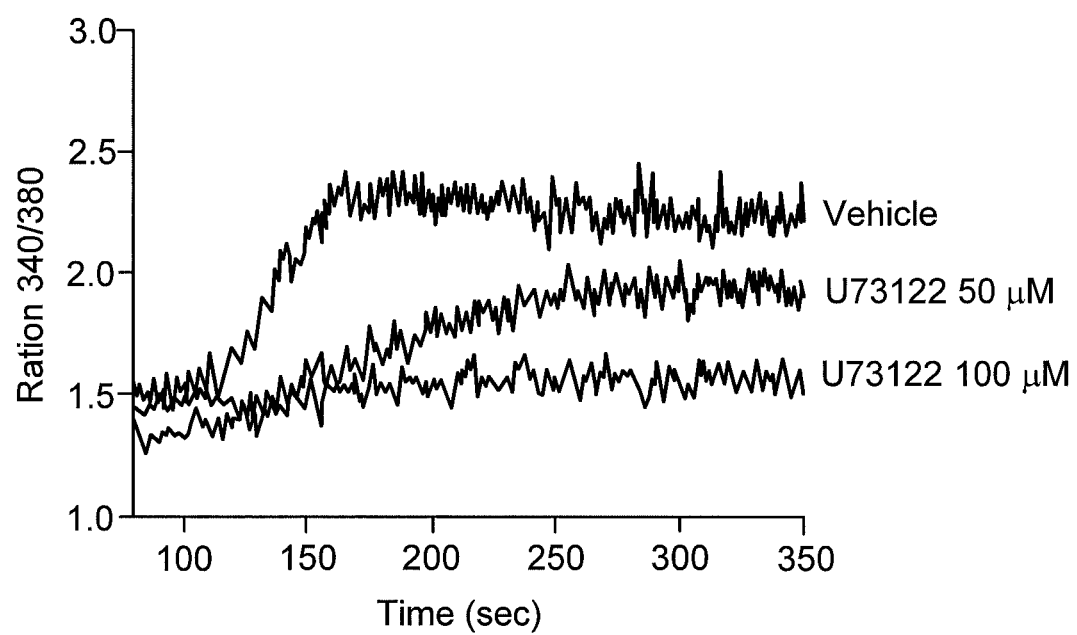
FIG. 3 shows the spectrofluorescence results for Jurkat T cells pretreated with U73122 100 µM or 50 µM, and treated with delphinidin 50 µM.

$4 \times 10^6$ FURA 2-AM-loaded Jurkat T cells were incubated in HBSS calcium free medium. The cells were then treated with vehicle alone or 50 or 100 uM U73122 for 10 minutes prior to incubation in 50 uM delphinidin. $Ca^{2+}$ flux was measured as ratio of excitation at 340 and 380 nm, and emission at 509 nm, at 37° C. in a spectrofluorimeter (LS55, PerkinElmer). As shown in FIG. 3, pretreatment with U73122 resulted in a dose-dependent reduction in delphinidin induced calcium flux that was not observed in cells treated with vehicle alone. These data suggested that delphinidin activation of T cells was mediated by phospholipase C and may involve activation of a membrane receptor.

Example 11: Delphinidin but not Cyanidin Induced Interleukin-2 Production in T Cells We explored the effect of delphinidin and cyanidin on interleukin-2 (IL-2) production in Jurkat T cells.

$2 \times 10^6$ Jurkat T cells in RPMI medium were incubated for 48 hrs at 37° C., in 5% $CO_2$ in the presence of vehicle control solution; or the T cell activator, phorbol 12-myristate 13-acetate/Ionomycin (PMA/Io 2 ng/ml 1 uM); 50 μM of delphinidin; 50 μM delphinidin+PMA/Io; 50 μM cyanidin; or 50 μM cyanidin+PMA/Io. Then the supernatants were collected and IL-2 production was analyzed by ELISA using a commercial kit (Becton Dickinson, USA) according to the supplier's directions.

TABLE 5

IL-2 production in samples of Jurkat T cells with different treatments.

| Treatment | Average IL-2 production [pg/ml] | Percentage vs. control [%] |
|---|---|---|
| Control samples | 50 | 100 |
| PMA/Io | 3750 | 7500 |
| 50 μM delphinidin | 170 | 340 |
| 50 μM delphinidin + PMA/Io | 3500 | 7000 |
| 50 μM cyanidin | 45 | 90 |
| 50 μM cyaniding + PMA/Io | 3700 | 7400 |

As shown in Table 5, delphinidin-treated cells produced significantly (P<0.05) higher levels of IL-2 (240% higher) than did the untreated control cells, while the cyanidin-treated cells produced slightly less IL-2 (10%) lower than did the control cells. These data suggested that delphinidin, but not cyanidin induced IL-2 production in Jurkat T cells.

As expected, the positive control PMA/Io induced high levels of IL-2 production. When delphinidin and cyanidin were added in combination with PMA/Io, both compounds reduced IL-2 production slightly.

Example 12: Delphinidin but not Cyanidin Induced Interferon-Gamma (INF-γ) Production in T Cells We also explored the effect of delphinidin and cyanidin on Interferon-gamma (INF-γ) production in Jurkat T cells. $2 \times 10^6$ Jurkat T cells in RPMI medium were incubated for 48 hrs at 37° C., in 5% $CO_2$. The samples were incubated in the presence of vehicle control solution; or the T cell activator, phorbol 12-myristate 13-acetate/Ionomycin (PMA/Io 2 ng/ml 1 uM); 50 µM of delphinidin; 50 µM delphinidin+ PMA/Io; 50 µM cyanidin; or 50 µM cyaniding+PMA/Io. Then the supernatants were collected and IFN-γ production was analyzed by ELISA using a commercial kit (Becton Dickinson, USA) according to the supplier's directions.

TABLE 6

INF-γ production in samples of Jurkat T cells with different treatments.

| Treatment | Average INF-γ production [pg/ml] | Percentage vs. control [%] |
|---|---|---|
| Control samples | 8 | 100 |
| PMA/Io | 60 | 750 |
| 50 µM delphinidin | 28 | 350 |
| 50 µM delphinidin + PMA/Io | 125 | 1562.5 |
| 50 µM cyanidin | 8 | 100 |
| 50 µM cyaniding + PMA/Io | 110 | 1375 |

As shown in Table 6, delphinidin-treated cells produced significantly ($P<0.05$) higher levels of INF-γ (250% higher) than did the untreated control cells, while the cyanidin-treated cells produced about the same levels of INF-γ as did the control cells. These data suggested that delphinidin, but not cyanidin induced INF-γ production in Jurkat T cells.

As expected, the positive control PMA/Io induced high levels of INF-γ production. In contrast to the effect on IL-2 production, when delphinidin and cyanidin were added in combination with PMA/Io, the compounds showed a syngergistic effect in INF-γ production, i.e., the levels of INF-γ were about twice that of cells treated with PMA/Io alone.

Example 13: Delphinidin Induced IL-2 and INF-γ in Human T Cells Via SOCE

The effect of delphinidin on IL-2 and INF-γ production was also assayed on freshly isolated human T cells. Human T cells were isolated from blood of healthy volunteers using Lymphoprep reagent. T cells ($1\times10^6$) in RMPI medium were incubated for 48 hrs at 37° C., in 5% $CO_2$ in the presence of a vehicle control solution; 50 µM delphinidin; 50 µM delphinidin+1 µM BTP-2; 50 µM delphinidin+5 µM BTP-2; 50 µM delphinidin+10 µM BTP-2; 1 µM BTP-2; 5 µM. BTP-2; or 10 µM BTP-2. Then the supernatants were collected and analyzed using commercial ELISA kit (Becton Dickinson, USA) to measure IL-2 and INF-γ production according to the supplier's directions.

TABLE 7

IL-2 production in samples of Human T cells with different treatments.

| Treatment | Average IL-2 production [pg/ml] |
|---|---|
| Control samples | 0 |
| 50 µM delphinidin | 370 |
| 50 µM delphinidin + 1 µM BTP-2 | 23 |
| 50 µM delphinidin + 5 µM BTP-2 | 20 |
| 50 µM delphinidin + 10 µM BTP-2 | 10 |
| 1 µM BTP-2 | 0 |
| 5 µM BTP-2 | 0 |
| 10 µM BTP-2 | 0 |

As shown in Table 7, delphinidin-treated human T cells produced significantly higher levels of IL-2 than did the untreated control cells. BTP-2 significantly ($P<0.05$) reduced the delphinidin-induced production of IL-2 at all concentrations tested. BTP_2 treatment alone did not induce IL-2 production.

TABLE 8

INF-γ production in samples of Human T cells with different treatments.

| Treatment | Average INF-γ production pg/ml] | Percentage vs. control [%] |
|---|---|---|
| Control samples | 370 | 100 |
| 50 µM delphinidin | 3900 | 1054.1 |
| 50 µM delphinidin + 1 µM BTP-2 | 550 | 148.6 |
| 50 µM delphinidin + 5 µM BTP-2 | 500 | 135.1 |
| 50 µM delphinidin + 10 µM BTP-2 | 150 | 40.5 |
| 1 µM BTP-2 | 240 | 64.9 |
| 5 µM BTP-2 | 390 | 105.4 |
| 10 µM BTP-2 | 140 | 37.8 |

As shown in Table 8, delphinidin-treated human T cells produced significantly ($P<0.05$) higher levels (950% higher) of INF-γ than did the untreated control cells. BTP-2 showed a dose-dependent reduction in the delphinidin-induced production of INF-γ at all concentrations tested. BTP_2 treatment alone did not induce IL-2 production.

Taken together, the data shown in Tables 7 and 8 suggest that delphinidin-induced IL-2 and INF-γ production was mediated in human T cells via a SOCE-dependent mechanism.

Example 14: Delphinidin Induced IL-2 Production Via Nuclear Factor of Activated T Cells (NFAT) Activation We then explored whether delphinidin induced IL-2 production via Nuclear Factor of Activated T cells (NFAT) activation. $2\times10^6$ Jurkat T cells in RPMI medium were incubated for 48 hrs at 37° C., in 5% $CO_2$, in the presence of a vehicle control solution; 50 µM delphinidin; 50 µM delphinidin+cyclosporin A (CsA, a calcineurin inhibitor of the NFAT pathway); or CsA alone. Then the supernatants were collected and analyzed using commercial ELISA kit (Becton Dickinson, USA) to measure IL-2 production according to the supplier's directions.

TABLE 9

IL-2 production in samples of Jurkat T cells inhibited by CsA.

| Treatment | Average IL-2 production [pg/ml] |
|---|---|
| Control samples | 0 |
| 50 µM delphinidin | 240 |
| 50 µM delphinidin + CsA | 10 |
| CsA | 0 |

As shown in Table 9, delphinidin-treated Jurkat T cells produced significantly higher levels of IL-2 than did the untreated control cells. CsA significantly reduced (($P<0.01$) the delphinidin-induced production of IL-2. No IL-2 production was detected in cell treated with CsA alone. The data shown in Table 9 suggested that delphinidin induced production of IL-2 in Jurkat T cells via NFAT activation.

Example 15: Effect of Andrographolide Plus Delphinidin on IL-2 Production in T Cells We evaluated the effect of a combination of delphinidin and andandrographolide on IL-2 production in both freshly harvested human T cells and the Jurkat cell line. Andrographolide was prepared according to the method described in Example 4. Human T cells were isolated from blood of healthy volunteers using Lymphoprep reagent. T cells ($1\times10^6$) in RMPI medium were incubated for 48 hrs at 37° C., in 5% $CO_2$ in the presence of a vehicle control solution; 5 nM andrographolide; 50 μM delphinidin; or 5 nM andrographolide plus 50 μM delphinidin. Then the supernatants were collected and analyzed using commercial ELISA kit (Becton Dickinson, USA) to measure IL-2 production according to the supplier's directions.

TABLE 10

IL-2 production in lymphocytes with different treatments.

| Treatment | Average IL-2 production [pg/ml] | Percentage compared to the control [%] |
|---|---|---|
| Control samples | 40 | 100 |
| 5 nM andrographolide | 85 | 212.5 |
| 50 μM delphinidin | 87 | 217.5 |
| 5 nM andrographolide + 50 μM delphinidin | 135 | 337.5 |

As shown in Table 10, andrographolide-treated and delphinidin-treated human T cells produced significantly higher levels (112% and 117% higher, respectively) of IL-2 than did the untreated control cells. Surprisingly, when andrographolide and delphinidin were added together, the two compounds showed a syngergistic effect in IL-2 production, i.e., the levels of IL-2 were 237% higher that those of cells treated with either andrographolide and delphinidin alone.

TABLE 11

IL-2 production in Jurkat T cells with different treatments.

| Treatment | Average IL-2 production [Abs 450 nm] | Percentage compared to the control [%] |
|---|---|---|
| Control samples | 0.0165 | 100 |
| 5 nM andrographolide | 0.0140 | 84.8 |
| 50 μM delphinidin | 0.023 | 139.4 |
| 5 nM andrographolide + 50 μM delphinidin | 0.0375 | 227.3 |

Jurkat T cells were incubated in either a vehicle control solution; 5 nM andrographolide; 50 μM delphinidin; or 5 nM andrographolide plus 50 μM delphinidin. As shown in Table 11, delphinidin-treated Jurkat T cells produced higher levels (39.4% higher) of IL-2 than did the untreated control cells; a slight reduction was observed with adrographolide. Surprisingly, when andrographolide and delphinidin were added together, the two compounds showed a syngergistic effect in IL-2 production, i.e., the levels of IL-2 were 127% higher that those of cells treated with either andrographolide and delphinidin alone.

Example 16: Anthocyanidins Interfered with Activation of NF-κB

We examined the effect of anthocyanidins on NF-κB activation using a luciferase reporter assay in HL-60 cells (Human promyelocytic leukemia cells). HL-60 cells in IMDM medium were transfected with a reporter vector with an NF-kB consensus sequence located in the luciferase promoter for 24 h at 37° C., then were incubated with delphinidin-rich anthocyanidins diluted 1:500000, 1:50000, and 1:5000. PMA was used as positive control. Luciferase activity was measured with a Dual luciferase assay kit (Promega) according to the supplier's instructions. A vector that constitutively expressed renilla luciferase was used to standardize the assay.

TABLE 12

Activity of NF-κB in HL-60 cells treated with different compositions of anthocyanidins rich in delphinidins compared to the control.

| Treatment | Average percentage activity of control [pNF-κB/pRL-luc] |
|---|---|
| Control samples | 100 |
| 1:500000 anthocyanidins rich in delphinidins | 73 |
| 1:50000 anthocyanidins rich in delphinidins | 62 |
| 1:5000 anthocyanidins rich in delphinidins | 43 |
| PMA | 50 |

As shown in Table 12, HL-60 luciferase transfectants showed a significant dose-dependent decrease in luciferase activity (at least three independent experiments, with a $P<0.05$). These data suggested that the activity of the anthocyanidins rich in delphinidins was mediated by NF-κB.

Example 17: Anti-Inflammatory Effect of Anthocyanidins in a In Vivo Model

A composition comprising anthocyanidins rich in delphinidins was prepared according to the present invention.

We assayed the effect of anthocyanidins on inflammation in vivo in an acute plantar inflammation model. Inflammation was induced in Sprague Dawley rats (200 g) using 1% carragenin (Sigma-Aldrich). The animals were treated with 35 mg/kg of anthocyanidins rich in delphinidins (prepared according to the method descirbed in Example 1) or with diclofenac (2 mg/kg). The diameter of the treated legs was measured with a digital caliper over 6 hrs. The area under the curve ($ABC_{0-6}$) was calculated; results are shown in Table 13.

TABLE 13

Area under the curve of the diameter of the treated legs.

| Treatment | Average $ABC_{0-6}$ [mm*hr] | Decrease percentage compared to control [%] |
|---|---|---|
| Control samples | 20 | 0 |
| Anthocyanidins rich in delphinidins 35 mg/kg | 13* | 35 |
| Diclofenac 2 mg/kg | 12.5** | 37.5 |

As shown in Table 13, treatment with anthocyanidins rich in delphinidins significantly reduced plantar edema (*$p<0.05$); this reduction was similar to that achieved with the positive control agent, diclofenac (**$p<0.01$).

Example 18: Effect of Anthocyanidins and Anthocyanidins Combined with Andrographolide on Cyclooxygenase 2 Expression We analyzed the effect of anthocyanidins and anthocyanidins combined with andrographolide on the expression of cyclooxygenase 2 (COX-2), an enzyme that mediates inflammatory processes. Caco-2 cells (a tumor line of colon cancer that constitutively expresses COX-2) were cultured in MEM medium, at 37° C. in 5% $CO_2$, and incubated with 1.75 μg/ml of delphinidin-rich for 24, 48 or 72 hours. Levels of COX-2 mRNA were analyzed by real-time RT_PCR using COX-2 specific primers using SYBRGreen reagent (Stratagene); β-actin served as an internal control. Levels of COX-2 protein were assayed by immunoblotting using a specific COX-2 antibody (Cayman) was performed to compare the expression; β-actin was used as standardized control.

Figure 4A:
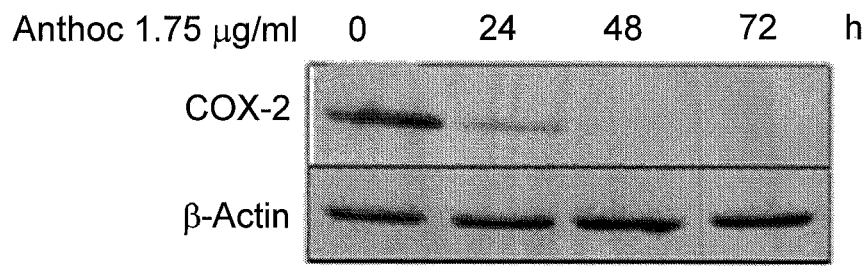
FIG. 4A shows COX-2 levels in an immunoblot of CaCo-2 cells treated with the composition comprising a final concentration in the samples of 1.75 µg/ml of anthocyanidins rich in delphinidins after 0, 24, 48, and 72 hrs.
Figure 4B:
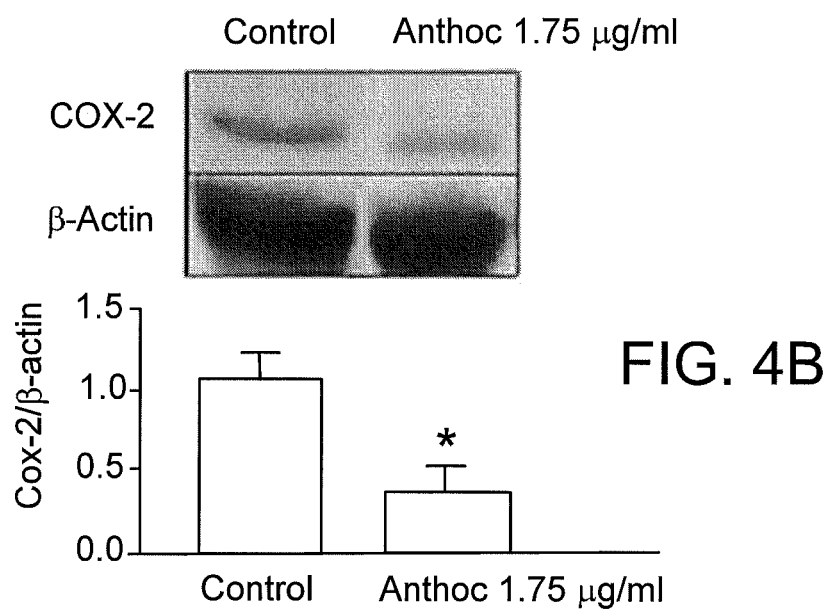
FIG. 4B shows RNAm COX-2 expression levels in a real time PCR of CaCo-2 cells treated with the composition comprising a final concentration in the samples of 1.75 µg/ml of anthocyanidins rich in delphinidins after 24 hrs.

FIG. 4A shows COX-2 polypeptide levels in an immunoblot of CaCo-2 cells treated with 1.75 μg/ml of delphinidin-rich anthocyanidins after 0, 24, 48, and 72 hrs. FIG. 4B shows COX-2 mRNA levels in CaCo-2 cells treated with 1.75 μg/ml of delphinidin-rich anthocyanidins for 24 hrs. As shown in FIG. 4A, treatment with 1.75 μg/ml of delphinidin-rich anthocyanidins for 24 hours reduced COX-2 polypeptide levels by about 50%; further reduction was observed at 48 and 72 hours. As shown in FIG. 4B, treatment with 1.75 μg/ml of delphinidin-rich anthocyanidins for 24 hours significantly reduced COX-2 mRNA levels to 50% of control levels.

Figure 4C:
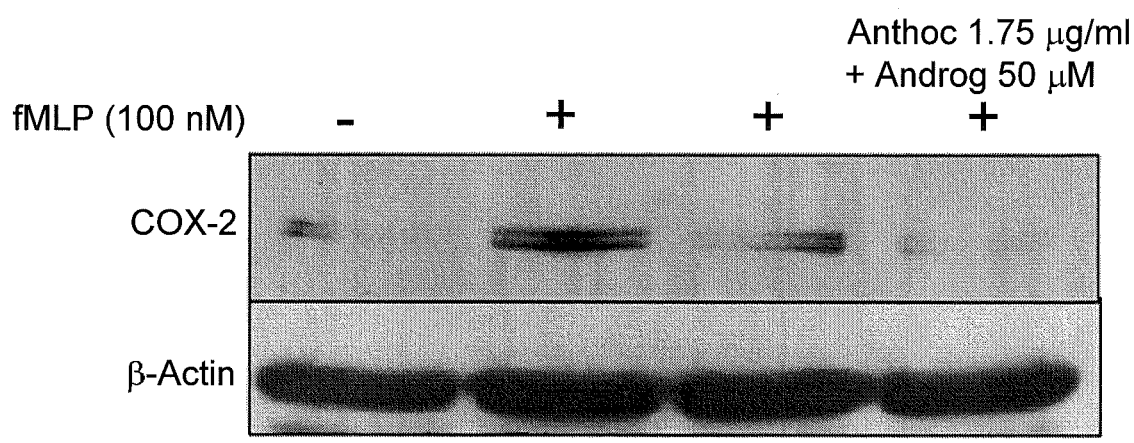
FIG. 4C shows COX-2 expression levels in an immunoblot of human neutrophils preincubated during 30 minutes with a composition according to the present invention considering a final concentration in the samples of 1.75 µM of anthocyanidins rich in delphinidins, or with a composition according to the present invention considering a final concentration in the samples of 1.75 µM of anthocyanidins rich in delphinidins and 50 µM andrographolides and treated with fMLP during 3 hours.

We also analyzed COX-2 polpeptide levels in human neutrophils. The cells were preincubated for 30 minutes with 1.75 μM of delphinidin-rich anthocyanidins or 1.75 μM of delphinidin-rich anthocyanidins and 50 μM andrographolides. The cells then treated for 3 hours with formyl-methionyl-leucyl-phenylalanine (fMLP) to induce COX-2 expression. COX-2 and β-actin polypeptide levels were assayed as described above. As shown in FIG. 4C, treatment with 1.75 μM of delphinidin-rich anthocyanidins reduced COX-2 polypeptide levels. Treatment with the combination of 1.75 μM of delphinidin-rich anthocyanidins and 50 μM andrographolides resulted in further reduction of COX-2 polypeptide.

Example 19: Effect of Anthocyanidins on PPAR-γ Activation

The ability of a group of drugs derived from thiazolidenediones (rosiglitazone and pioglitazone) to regulate the level of glycemia via activation of PPar-γ (peroxisome proliferator-activated receptor, a receptor involved in sensitization to insulin) is known. In addition to altering the expression levels of adipokines, proinflammatory proteins and lipids, activation of PPar-γ also produces sensitization to insulin, without increase of adipogenesis (Sugii et al., 2009), of mature adipocytes. Therefore, the activation of PPar-γ could prevent the development of type II diabetes and improve the response to insulin.

We examined the effect of delphindin-rich anthocyanidins on PPAR-γ activation. HL-60 cells in IMDM medium were transfected with the reporter vectors PPAR-γ-Luc (5 μg) (Panomics) and TK-RL (1 μg) (Promega) using Fugene 6 reagent (Roche), and cultured for 24 hr. Then, the cells were incubated for 12 h in 0.175, 1.75, or 17.5 μg/ml of delphindin-rich anthocyanidins, phorbol myristate acetate (PMA), 15-deoxi-d 12,14-prostaglandin J2 (PGj2), or tumor necrosis factor alpha (TNFα) as controls. Luciferase activity was measured using the Dual-Luciferase Reporter Assay kit (DLR) from Promega in a luminometer (Luminoskan).

TABLE 14

Activation of PPar-γ with different compositions (anth = anthocyanidins).

| Treatment | Average percentage activity of control [PPAR-γ-Luc/TK-RL] ± SD |
|---|---|
| Control samples | 100 |
| 0.175 μg/ml anth rich in delphinidins | 346.7 ± 450.6 |
| 1.75 μg/ml anth rich in delphinidins | 285.7 ± 171.5 |
| 17.5 μg/ml anth rich in delphinidins | 706.7 ± 829.9 |
| PMA | 527.5 ± 536.3 |
| PGj2 | 256.8 ± 126.9 |
| TNFα | 283.4 ± 47.23 |

Figure 5:
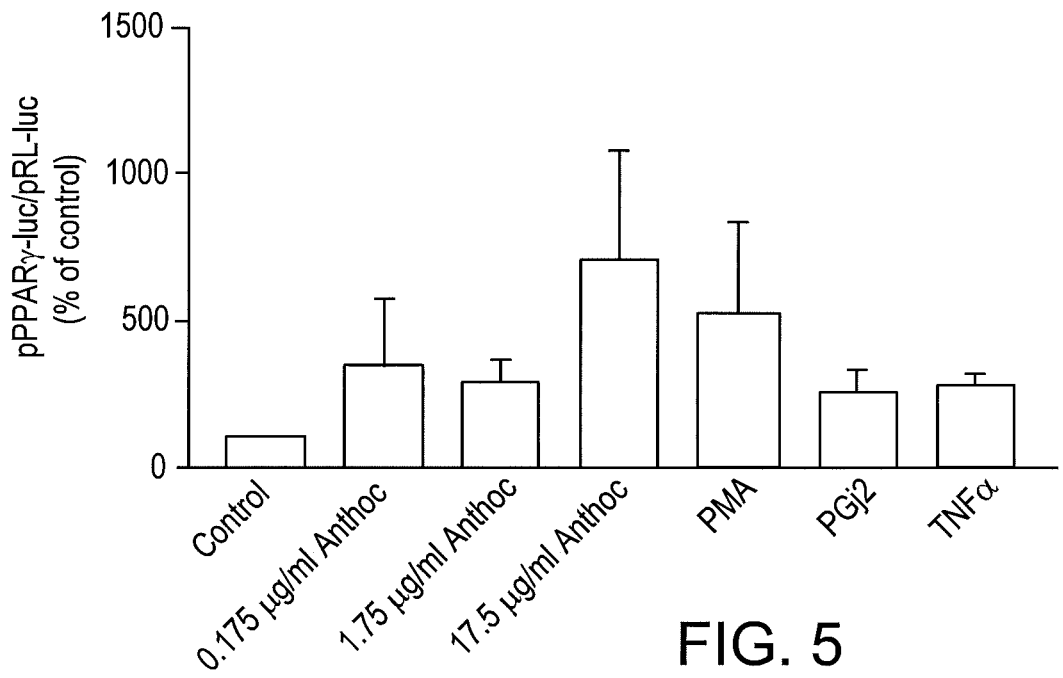
FIG. 5 shows PPar-γ activation compared to the control in HL-60 cells transfected with a reporter vector PPar-γ-Luc, and treated with a composition according to the invention comprising final concentrations in the samples of 0.175 µg/ml, 1.75 µg/ml, 17.5 µg/ml anthocyanidins rich in delphinidins, or treated with PMA, PGj2 or TNFα for 12 hrs.

As shown in Table 14, the positive controls, PMA, PGj2 and TNF-α increased luciferase activity in PPAR-γ-Luc transfected HL-60 cells. Treatment with delphinidin-rich anthocyanidins produced a dose-dependent increase in luciferase activity. These data are represented graphically in FIG. 5. These data suggest that because delphinidin-rich anthocyanidins increased PPAR-γ activity, such compounds may provide a therapeutic benefit in type II diabetes.

Example 20: Effects of Delphinidin-Rich Anthocyanidins on Hyperglycemia in Diabetic Rats We evaluated the effect of delphinidin-rich anthocyanidins in a diabetic rat model. Diabetes was induced in rats by endovenous injection of streptozotocin. After 7 days the metabolic profiles of the animals were analyzed to determine which rats were hyperglycemic. The hyperglycemic rats were randomly assigned to different groups: a water-treated control group, a group treated with 7 mg/kg of delphinidin-rich anthocyanidins; and group treated with 70 mg/kg of delphinidin-rich anthocyanidins. Each group consisted of 5 rats. The rats were treated for two weeks with the delphinidin-rich anthocyanidins mixed in the drinking water of the rats. After two weeks of treatment, 1 ml of blood was obtained from each animal by retro-orbital puncture. The glycemia level was determined in the blood with glucose oxidase method (Wiener-Lab).

TABLE 15

Glycemia level in diabetic rats treated with compositions of the invention.

| Treatment | Average glycemia increase level [mg/dl] | Decrease percentage compared to control [%] |
|---|---|---|
| Control samples | 195 | 0 |
| Anthocyanidins rich in delphinidins 7 mg/kg | 62* | 68.2 |
| Anthocyanidins rich in delphinidins 70 mg/kg | 190 | 2.6 |

$p < 0.05$

Figure 6:
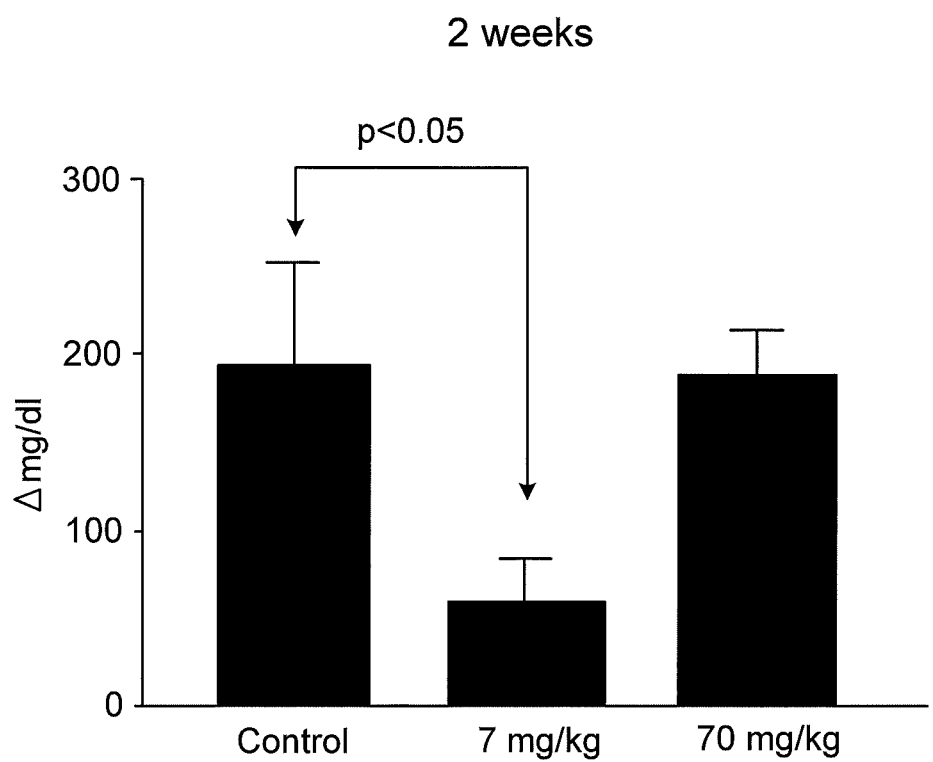
FIG. 6 shows the results for glycemia increase levels in the three groups of treatment of rats: control group, treated with water; group treated with a composition according to the invention considering a dose of 7 mg/kg of anthocyanidins rich in delphinidins; and group treated with a composition according to the invention considering a dose of 70 mg/kg of anthocyanidins rich in delphinidins; and the effecrof the compositions according to the invention for reducing this increased levels.

An increase of approximately 200 mg/dl of glycemia was observed in the diabetic animals compared to the levels prior to streptozotocin. As shown in Table 15, animals treated with a dose of 7 mg/kg delphinidin-rich anthocyanidins in hyglycemia showed a significant reduction (p<0.05) in hypoglycemia; interestingly, animals treated with the higher dose 70 mg/kg delphinidin-rich anthocyanidins had glycemia levels that were nearly identical to those of control animals. These data are represented graphically in FIG. 6.

Example 21: Formulation of a Composition Comprising Delphinidin-Rich Anthocyanidins into Hard Gelatin Capsules Within a unit composition:

| | |
|---|---|
| Composition comprising anthocyanidins (41% anthocyanidins, 35% of this anthocyanidins are delphinidins) | 400 mg |
| Microcrystalline cellulose | 400 mg |
| Lactose | 95 mg |
| Silicon dioxide | 10 mg |

In this Example and the Examples that follow which describe certain amounts of the various components of the invention, the invention encompasses similar compositions in which the amounts provided for one or more of the components vary, for example, by plus-or-minus about 10%. Thus, the invention encompasses compositions comprising the components listed above in which, for example, the anthocyanin/anthocyanidin is present at 360-440 mg.

Example 22: Formulation of a Composition Comprising Andrographolides and Delphinidin-Rich Anthocyanidins (Ratio 3:1) into an Oily Suspension for Soft Cellulose Capsules Within a unit composition:

| | |
|---|---|
| Composition comprising andrographolides (35% total andrographolides) | 300 mg |
| Composition comprising anthocyanidins (41% anthocyanidins, 35% of this anthocyanidins are delphinidins) | 100 mg |
| Glyceryl monostearate | 30 mg |
| Soya lecithin | 20 mg |
| *Oenothera biennis* oil q.s. for | 700 mg |

Example 23: Formulation of a Composition Including a Composition Comprising Andrographolides and Delphinidin-Rich Anthocyanidins (Ratio 3:1) into Hard Gelatin Capsules Within a unit composition:

| | |
|---|---|
| Composition comprising andrographolides (35% total andrographolides) | 300 mg |
| Composition comprising anthocyanidins (41% anthocyanidins, 35% of this anthocyanidins are delphinidins) | 100 mg |
| Microcrystalline cellulose | 400 mg |
| Lactose | 95 mg |
| Silicon dioxide | 10 mg |

Example 24: Formulation of a Composition Comprising Andrographolides and Delphinidin-Rich Anthocyanidins (Ratio 1:1) into Hard Gelatin Capsules Within a unit composition:

| | |
|---|---|
| Composition comprising andrographolides (35% total andrographolides) | 200 mg |
| Composition comprising anthocyanidins (41% anthocyanidins, 35% of this anthocyanidins are delphinidins) | 200 mg |
| Microcrystalline cellulose | 400 mg |
| Povidone | 15 mg |
| Sodium carboxymethylcellulose | 10 mg |

Example 25: Formulation of a Composition Comprising Delphinidin-Rich Anthocyanidins and a Caffeeoylquinic Acid (Ratio 1:1) into Hard Gelatin Capsules Within a unit composition:

| | |
|---|---|
| Composition comprising caffeeoylquinic acid (20% cafeeoylquinic acid) | 200 mg |
| Composition comprising anthocyanidins (41% anthocyanidins, 35% of this anthocyanidins are delphinidins) | 200 mg |
| Microcrystalline cellulose | 400 mg |
| Lactose | 95 mg |
| Silicon dioxide | 10 mg |

Example 26: Chromatographic Analysis of Delphinidin-Rich Anthocyanidins

A chromatographic analysis of a composition comprising delphinidin-rich anthocyanidins was performed.

TABLE 16

Peaks table of content of anthocyanidins of a composition comprising anthocyanidins rich in delphinidins according to the invention.

| | Name | RT [min] | RRT | Area [uV*sec] | Content [%] |
|---|---|---|---|---|---|
| 1 | Delphinidin-3-O-samb-5-O-gluc | 19.164 | 0.640 | 2367620 | 6.38 |
| 2 | Delphinidin-3,5-O-diglucos | 20.117 | 0.672 | 6057231 | 13.64 |
| 3 | Cyanidin-3-O-samb-5-O-gluc | 22.506 | 0.752 | 1268598 | 3.36 |
| 4 | Cyanidin-3,5-O-diglucos | 22.852 | 0.764 | 721117 | 1.58 |
| 5 | Delphinidin-3-O-sambubioside | 24.410 | 0.816 | 774162 | 1.67 |
| 6 | Delphinidin-3-O-glucoside | 25.871 | 0.864 | 4108076 | 6.95 |
| 7 | Cyanidin-3-O-sambubioside | 28.996 | 0.969 | 377697 | 0.79 |
| 8 | Cyanidin-3-O-glucoside | 29.930 | | 639701 | 1.05 |
| | Sum of contents | | | | 35.42 |

As shown in Table 16, 35.45% of the content of the composition corresponds to anthocyanidins, from which 28.64% are delphinidins and 6.78% were cyanidins. Although it was not the most abundant, a high content of delphinidin-3-O-sambubioside-5-O-glucoside was observed. This content corresponds to 6.38% of the total contents, 18% of the content of anthocyanidins, and 22.3% of the content of delphinidins. Delphinidin-3-O-sambubioside-5-O-glucoside was a particular characteristic component of the compositions of the invention.

Example 27: Effect of Maqui Extracts Combined with *Vaccinium* or *A. paniculata* Extracts on Blood Glucose Levels in a Diabetic Rat Model We compared the effect of oral administration of Maqui extract alone, with Maqui extract combined with extract from *Vaccinium* or *A. paniculata* in a diabetic rat model. Rats were treated with streptozotocin at 60 mg/kg to induce diabetes. One week after streptozotocin administration, the animals were divided into five groups that each received the following treatment: 1) Group 1, (n=5), untreated diabetic control; 2) Group 2 (n=4), Maqui (20 mg/kg); 3) Group 3, (n=5), Maqui (200 mg/kg); 4) Group 4 (n=4), Maqui (20 mg/kg) plus *Vaccinium* (100 mg/kg); 5) Group 5 (n=5), Maqui (20 mg/kg) plus *A. paniculata* (100 mg/kg). After four days of treatment, blood samples were taken and blood glucose levels were measured using an ACCU-CHEK® kit (Roche) according to the supplier's instructions.

The Maqui extract was standardized extract of fresh maqui fruit (35% of total anthocianins, min: total delphinidins 25%: min. delphinidin DSG: 5%); the *A. paniculata* extract was from dried herba (37% total andrographolides, with approximately 20 to 40% w/w of Andrographolide, about 5 to 10% w/w of 14-Deoxyandrographolide, and about 0.2 to 0.8% w/w of Neoandrographolide. *Vaccinium angustifolium* extract was a: standardized extract of dried leaves (chorogenic acid 16%).

The post-treatment mean blood sugar levels were: 1) Group 1, untreated diabetic control 361.2±107.98 (SEM=48.29); 2) Group 2, Maqui (20 mg/kg), 354±176.71 (SEM=88.35); 3) Group 3, Maqui (200 mg/kg) 383.2±137.35 (SEM=61.42); 4) Group 4, Maqui (20 mg/kg) plus *Vaccinium* (100 mg/kg), 261.5±99.71 (SEM=49.85); 5) Group 5, Maqui (20 mg/kg) plus *A. paniculata* (100 mg/kg) 223.4±120.56 (SEM=53.92). These data suggested that combining Maqui extract with extract from either *Vaccinium* or *A. paniculata* reduced blood sugar levels to a greater degree than did Maqui extract alone.

A number of embodiments of the invention have been described. Nevertheless, it will be understood that various modifications may be made without departing from the spirit and scope of the invention. For example, the botanical extracts that include an anthocyanidin can be made from any botanical that includes such compounds (e.g., plants of the genus *Ribes, Vitis,* and *Sambucus,* as well as the *Aristotelia* and *Vaccinium* plants described at length above). Accordingly, other embodiments are within the scope of the invention and the following claims.

What is claimed is:

1. A pharmaceutical composition comprising:
   a first composition comprising a carrier; and
   about 100 mg to 400 mg of a second composition comprising a plurality of anthocyanins and anthocyanidins, wherein the plurality of anthocyanins and anthocyanidins constitute at least about 35% by weight of the second composition, wherein the 35% by weight is distributed between delphinidin-3-O-sambubioside-5-O-glucoside, delphinidin-3,5-O-diglucoside, cyanidin-3,5-O-diglucoside, dephinidin-3-O-O-sambubioside-5-O-glucoside, cyanidin-3-O-sambubioside, and cyanidin-3-O-glucoside; and wherein at least about 15% of the plurality of anthocyanins or anthocyanidins or both are sugar-free or sugar-containing delphinidins, wherein the pharmaceutical composition is formulated as a soft cellulose capsule or hard gelatin capsule.

2. The pharmaceutical composition of claim 1, wherein the first composition comprises microcrystalline cellulose, lactose, silicon dioxide, glyceryl monostearate, soya lecithin, or *Oenothera biennis* oil.

3. The pharmaceutical composition of claim 1, wherein about 35%-45% of the second composition is anthocyanins or anthocyanidins or both and about 15%-50% of the anthocyanins or anthocyanidins or both are sugar-free or sugar-containing delphinidins.

4. The pharmaceutical composition of claim 1, further comprising a third composition comprising an andrographolide.

5. The pharmaceutical composition of claim 4, wherein about 30%-40% of the third composition is an andrographolide.

6. The pharmaceutical composition of claim 4, wherein the ratio of the second composition to the third composition comprising is about 1.0:0.5 to 1.0:3.0 (w:w).

* * * * *